US012767699B2

(12) United States Patent
Putyrski et al.

(10) Patent No.: US 12,767,699 B2
(45) Date of Patent: Oct. 20, 2026

(54) PD-L1 VARIANTS WITH IMPROVED AFFINITY TOWARDS PD-1

(71) Applicant: Fraunhofer-Gesellschaft zur Förderung der angewandten Forschung e.V., Munich (DE)

(72) Inventors: Mateusz Putyrski, Munich (DE); Andreas Ernst, Munich (DE); Svenja Wiechmann, Munich (DE); Andreas Von Knethen, Munich (DE); Michael John Parnham, Munich (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 1028 days.

(21) Appl. No.: 17/997,471

(22) PCT Filed: Apr. 29, 2021

(86) PCT No.: PCT/EP2021/061308

§ 371 (c)(1),
(2) Date: Oct. 28, 2022

(87) PCT Pub. No.: WO2021/219807

PCT Pub. Date: Nov. 4, 2021

(65) Prior Publication Data

US 2023/0174619 A1 Jun. 8, 2023

(30) Foreign Application Priority Data

Apr. 30, 2020 (EP) .................................... 20172388

(51) Int. Cl.

| | |
|---|---|
| ***C07K 14/705*** | (2006.01) |
| ***A61K 38/00*** | (2006.01) |
| ***A61P 29/00*** | (2006.01) |
| ***A61P 37/00*** | (2006.01) |

(52) U.S. Cl.

CPC ........ *C07K 14/70596* (2013.01); *A61P 29/00* (2018.01); *C07K 2319/30* (2013.01)

(58) Field of Classification Search

None

See application file for complete search history.

(56) References Cited

U.S. PATENT DOCUMENTS

| | | | | |
|---|---|---|---|---|
| 8,039,589 | B1 | 10/2011 | Chen | |
| 10,632,174 | B2 * | 4/2020 | Von Knethen | A61K 39/395 |
| 11,679,142 | B2 * | 6/2023 | Von Knethen | A61K 47/6835 424/134.1 |
| 2013/0017199 | A1 * | 1/2013 | Langermann | A61P 35/02 424/134.1 |
| 2014/0341917 | A1 * | 11/2014 | Nastri | A61P 15/00 435/69.6 |
| 2016/0011204 | A1 * | 1/2016 | Almo | G01N 33/54366 506/14 |
| 2019/0153065 | A1 * | 5/2019 | Garrett-Thomson | A61P 37/06 |
| 2019/0352404 | A1 * | 11/2019 | Xu | G01N 33/68 |
| 2020/0299353 | A1 * | 9/2020 | Berry | C07K 14/70532 |
| 2021/0261667 | A1 * | 8/2021 | Wan | A61P 35/00 |

FOREIGN PATENT DOCUMENTS

| | | | |
|---|---|---|---|
| EP | 3572429 | A1 | 11/2019 |
| JP | 2020506908 | A | 3/2020 |
| WO | 2017/029389 | A1 | 2/2017 |
| WO | 2017/201131 | A1 | 11/2017 |
| WO | 2020/080672 | A1 | 4/2020 |

OTHER PUBLICATIONS

Chen et al. (2023) Front. Immunol. 14:1323797, p. 1-17.*

Jiang et al. (2019) Human Vaccines & Immunotherapeutics, 15:5, 1111-1122.*

Gantz et al. (2024) On synergy between ultrahigh throughput screening and machine learning in biocatalyst engineering. Faraday Discuss., 252: 89-114.*

Jiang et al. (2023) Fluorescence coupling strategies in fluorescence-activated droplet sorting (FADS) for ultrahigh-throughput screening of enzymes, metabolites, and antibodies. Biotechnology Advances, 66: 108173; p. 1-20.*

Liu et al. (2023) Advances in ultrahigh-throughput screening technologies for protein evolution. Trends in Biotechnology, 41(9):1168-1181.*

Wang, Shengdian et al., "Molecular modeling and functional mapping of B7-H1 and B7-DC uncouple costimulatory function from PD-1 interaction", The Journal of Experimental Medicine, Rockefeller University Press, US, vol. 197, No. 9, May 5, 2003 (May 5, 2003), pp. 1083-1091, XP002517347.

Database UniProt [Online] May 10, 2017 (May 10, 2017), "SubName: Full=programmed cell death 1 ligand 1 isoform X1 {ECO:00003131 RefSeq:XP _005063766.1, ECO:0000313IRefSeq:XP _021080847. 1}".

Shi, Danfeng et al., "Understanding the structural and energetic basis of PD-1 and monoclonal antibodies bound to PD-L 1: A molecular modeling perspective", Biochimica Et Biophysica Acta (BBA)—General Subjects, Elsevier, Amsterdam, NL, vol. 1862, No. 3, Dec. 2, 2017 (Dec. 2, 2017), pp. 576-588, XP085414881.

Wang, Kai et al., "Effect of the hairpin structure of peptide inhibitors on the blockade of PD-1 /PD-L 1 axis" Biochemical and Biophysical Research Communications, vol. 527, No. 2, Apr. 23, 2020 (Apr. 23, 2020), pp. 453-457, XP055731878.

(Continued)

*Primary Examiner* — Ilia I Ouspenski

(74) *Attorney, Agent, or Firm* — SAFFIRE IP; Daren P Nicholson

(57) ABSTRACT

The present invention relates to a PD-L1 polypeptide comprising at least a first amino acid sequence at least 70% identical to SEQ ID NO:8, and at least a second sequence at least 70% identical to SEQ ID NO: 10, wherein the polypeptide carries amino acid substitutions at least at the amino acid positions Y56 and P76, wherein the amino acid positions are based on the murine PD-L1 amino acid sequence (SEQ ID NO:6). The present invention also relates to a polynucleotide encoding the aforesaid PD-L1 polypeptide, and to host cells, methods, and uses related thereto.

15 Claims, 10 Drawing Sheets

Figure 1:
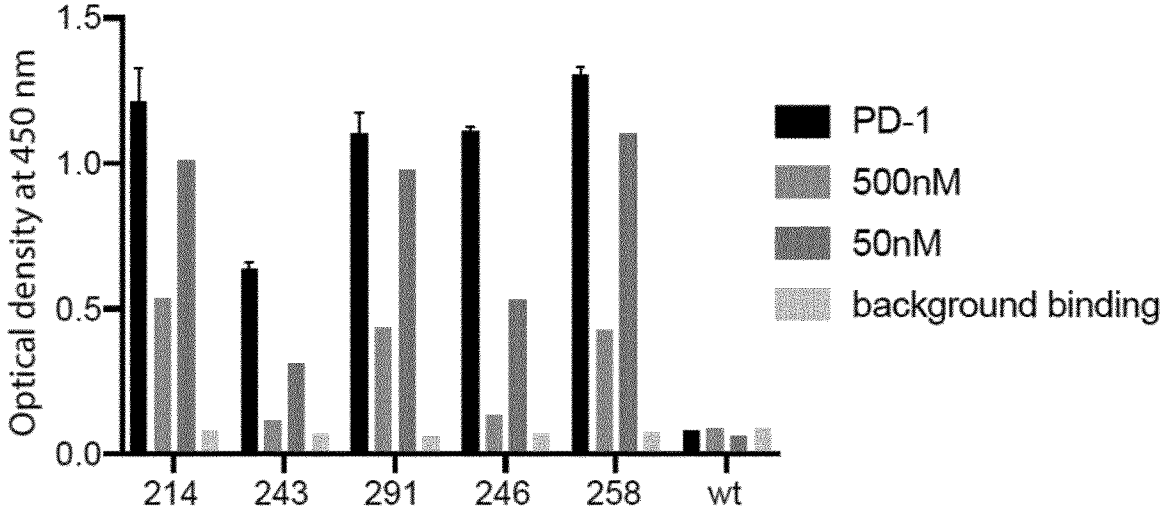

Specification includes a Sequence Listing.

(56) References Cited

OTHER PUBLICATIONS

PCT/EP2021/061308 Written Opinion of the International Searching Authority, EPO, Munich, DE, Jul. 21, 2021.
PCT/EP2021/061308 International Search Report, EPO, Risjwijk, NL, Jul. 21, 2021.
Hotchkiss and Opal, "Immunotherapy for Sepsis: a new approach against an ancient foe," (2010) N Engl J Med 363:87-89.
Meisel et al., "Granulocyte-Macrophage Colony-stimulating Factor to Reverse Sepsis-associated Immunosuppression A Double-Blind, Randomized, Placebo-controlled Multicenter Trial," (2009) Am J Respir Crit Care Med 180:640-648.
Otto et al., "The late phase of sepsis is characterized by an increased microbiological burden and death rate, " (2011) Crit Care 15:RI83.
Reinhart et al., "Anti-tumor necrosis factor therapy in sepsis: Update on clinical trials and lessons learned," (2001) Crit Care Med 29:765-769 Abstract.
Vincent et al., "Sepsis definitions: time for change," (2013) Lancet 381:774-775.
Von Knethen et al., "Tolerizing CTL by Sustained Hepatic PD-L1 Expression Provides a New Therapy Approach in Mouse Sepsis," (2019), Theranostics 9(7):2003.
Reinhart et al., "Randomized, placebo-controlled trial of the anti-tumor necrosis factor antibody fragment afelimomab in hyperinflammatory response during severe sepsis: The RAMSES Study," (2001) Crit Care Med 29:765-769.

* cited by examiner

A

C

B

A

B

SEQUENCE LISTING

```
<160> NUMBER OF SEQ ID NOS: 26

<210> SEQ ID NO 1
<211> LENGTH: 348
<212> TYPE: DNA
<213> ORGANISM: Mus musculus

<400> SEQUENCE: 1

gcgtttacta tcacggctcc aaaggacttg tacgtggtgg agtatggcag caacgtcacg      60

atggagtgca gattccctgt agaacgggag ctggacctgc ttgcgttagt ggtgtactgg     120

gaaaaggaag atgagcaagt gattcagttt gtggcaggag aggaggacct taagcctcag     180

cacagcaact tcaggggggag agcctcgctg ccaaaggacc agcttttgaa gggaaatgct     240

gcccttcaga tcacagacgt caagctgcag gacgcaggcg tttactgctg cataatcagc     300

tacggtggtg cggactacaa gcgaatcacg ctgaaagtca atgcccca                  348

<210> SEQ ID NO 2
<211> LENGTH: 348
<212> TYPE: DNA
<213> ORGANISM: Homo sapiens

<400> SEQUENCE: 2

gcatttactg tcacggttcc caaggaccta tatgtggtag agtatggtag caatatgaca      60

attgaatgca aattcccagt agaaaaacaa ttagacctgg ctgcactaat tgtctattgg     120

gaaatggagg ataagaacat tattcaattt gtgcatggag aggaagacct gaaggttcag     180

catagtagct acagacagag ggcccggctg ttgaaggacc agctctccct gggaaatgct     240

gcacttcaga tcacagatgt gaaattgcag gatgcagggg tgtaccgctg catgatcagc     300

tatggtggtg ccgactacaa gcgaattact gtgaaagtca atgcccca                  348

<210> SEQ ID NO 3
<211> LENGTH: 873
<212> TYPE: DNA
<213> ORGANISM: Mus musculus

<400> SEQUENCE: 3

atgaggatat ttgctggcat tatattcaca gcctgctgtc acttgctacg ggcgtttact      60

atcacggctc caaaggactt gtacgtggtg gagtatggca gcaacgtcac gatggagtgc     120

agattccctg tagaacggga gctggacctg cttgcgttag tggtgtactg ggaaaaggaa     180

gatgagcaag tgattcagtt tgtggcagga gaggaggacc ttaagcctca gcacagcaac     240

ttcaggggga gagcctcgct gccaaaggac cagcttttga agggaaatgc tgcccttcag     300

atcacagacg tcaagctgca ggacgcaggc gtttactgct gcataatcag ctacggtggt     360

gcggactaca agcgaatcac gctgaaagtc aatgccccat accgcaaaat caaccagaga     420

atttccgtgg atccagccac ttctgagcat gaactaatat gtcaggccga gggttatcca     480

gaagctgagg taatctggac aaacagtgac caccaacccg tgagtgggaa gagaagtgtc     540
```

```
accacttccc ggacagaggg gatgcttctc aatgtgacca gcagtctgag ggtcaacgcc    600

acagcgaatg atgttttcta ctgtacgttt tggagatcac agccagggca aaaccacaca    660

gcggagctga tcatcccaga actgcctgca acacatcctc cacagaacag gactcactgg    720

gtgcttctgg gatccatcct gttgttcctc attgtagtgt ccacggtcct cctcttcttg    780

agaaaacaag tgagaatgct agatgtggag aaatgtggcg ttgaagatac aagctcaaaa    840

aaccgaaatg atacacaatt cgaggagacg taa                                 873


<210> SEQ ID NO 4
<211> LENGTH: 116
<212> TYPE: PRT
<213> ORGANISM: Mus musculus

<400> SEQUENCE: 4

Ala Phe Thr Ile Thr Ala Pro Lys Asp Leu Tyr Val Val Glu Tyr Gly
1               5                   10                  15

Ser Asn Val Thr Met Glu Cys Arg Phe Pro Val Glu Arg Glu Leu Asp
            20                  25                  30

Leu Leu Ala Leu Val Val Tyr Trp Glu Lys Glu Asp Glu Gln Val Ile
        35                  40                  45

Gln Phe Val Ala Gly Glu Glu Asp Leu Lys Pro Gln His Ser Asn Phe
    50                  55                  60

Arg Gly Arg Ala Ser Leu Pro Lys Asp Gln Leu Leu Lys Gly Asn Ala
65                  70                  75                  80

Ala Leu Gln Ile Thr Asp Val Lys Leu Gln Asp Ala Gly Val Tyr Cys
                85                  90                  95

Cys Ile Ile Ser Tyr Gly Gly Ala Asp Tyr Lys Arg Ile Thr Leu Lys
            100                 105                 110

Val Asn Ala Pro
        115


<210> SEQ ID NO 5
<211> LENGTH: 116
<212> TYPE: PRT
<213> ORGANISM: Homo sapiens

<400> SEQUENCE: 5

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro
        115


<210> SEQ ID NO 6
```

<211> LENGTH: 290
<212> TYPE: PRT
<213> ORGANISM: Mus musculus

<400> SEQUENCE: 6

```
Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290
```

<210> SEQ ID NO 7
<211> LENGTH: 23
<212> TYPE: PRT
<213> ORGANISM: Mus musculus

<400> SEQUENCE: 7

```
Val Val Tyr Trp Glu Lys Glu Asp Glu Gln Val Ile Gln Phe Val Ala
1               5                   10                  15

Gly Glu Glu Asp Leu Lys Pro
            20
```

<210> SEQ ID NO 8

<211> LENGTH: 23
<212> TYPE: PRT
<213> ORGANISM: Homo sapiens

<400> SEQUENCE: 8

```
Ile Val Tyr Trp Glu Met Glu Asp Lys Asn Ile Ile Gln Phe Val His
1               5                   10                  15

Gly Glu Glu Asp Leu Lys Val
            20
```

<210> SEQ ID NO 9
<211> LENGTH: 13
<212> TYPE: PRT
<213> ORGANISM: Mus musculus

<400> SEQUENCE: 9

```
Cys Cys Ile Ile Ser Tyr Gly Gly Ala Asp Tyr Lys Arg
1               5                   10
```

<210> SEQ ID NO 10
<211> LENGTH: 13
<212> TYPE: PRT
<213> ORGANISM: Homo sapiens

<400> SEQUENCE: 10

```
Arg Cys Met Ile Ser Tyr Gly Gly Ala Asp Tyr Lys Arg
1               5                   10
```

<210> SEQ ID NO 11
<211> LENGTH: 345
<212> TYPE: DNA
<213> ORGANISM: Artificial Sequence
<220> FEATURE:
<223> OTHER INFORMATION: clone 214 encoding

<400> SEQUENCE: 11

```
gcgtttacta tcacggctcc aaaggacttg tacgtggtgg agtatggcag caacgtcacg     60

atggagtgca gattccctgt agaacgggag ctggacctgc ttgcgttatt ggtggactgg    120

gaaaaggaag atgagcaagt gattcgattt gagtcaggag aggaggacct taagcatcag    180

cacagcaact tcagggggag agcctcgctg ccaaaggacc agcttttgaa gggaaatgct    240

gcccttcaga tcacagacgt caagctgcag gacgcaggcg tttaccgctg cataatcagc    300

tacggtggtg cggactacaa gcgaatcacg ctgaaagtca atgcc                    345
```

<210> SEQ ID NO 12
<211> LENGTH: 345
<212> TYPE: DNA
<213> ORGANISM: Artificial Sequence
<220> FEATURE:
<223> OTHER INFORMATION: clone 258 encoding

<400> SEQUENCE: 12

```
gcgtttacta tcacggctcc aaaggacttg tacgtggtgg agtatggcag caacgtcacg     60

atggagtgca gattccctgt agaacgggag ctggacctgc ttgcgttagt agtgtcctgg    120

gaaaaggaag atgagcaagt gattcagttt gtggccggag aggaggacct taagtttcag    180

cacagcaact tcagggggag agcctcgctg ccaaaggacc agcttttgaa gggaaatgct    240

gcccttcaga tcacagacgt caagctgcag gacgcaggcg tttacaggtg cctaatcagc    300

tacggtggtg cggactacaa gcgaatcacg ctgaaagtca atgcc                    345
```

<210> SEQ ID NO 13
<211> LENGTH: 345
<212> TYPE: DNA
<213> ORGANISM: Artificial Sequence
<220> FEATURE:
<223> OTHER INFORMATION: clone 243 encoding

<400> SEQUENCE: 13
gcgtttacta tcacggctcc aaaggacttg tacgtggtgg agtatggcag caacgtcacg 60
atggagtgca gattccctgt agaacgggag ctggacctgc ttgcgttagt cgtggcctgg 120
gaaaaggaag atgagcacgt gattcagttt gttacaggag aggaggacct taagtttcag 180
cacagcaact tcagggggag agcctcgctg ccaaaggacc agcttttgaa gggaaatgct 240
gcccttcaga tcacagacgt caagctgcag gacgcaggcg tttaccgctg cataatcagc 300
tacggtggtg cggactacaa gcgaatcacg ctgaaagtca atgcc 345

<210> SEQ ID NO 14
<211> LENGTH: 345
<212> TYPE: DNA
<213> ORGANISM: Artificial Sequence
<220> FEATURE:
<223> OTHER INFORMATION: clone 246 encoding

<400> SEQUENCE: 14
gcgtttacta tcacggctcc aaaggacttg tacgtggtgg agtatggcag caacgtcacg 60
atggagtgca gattccctgt agaacgggag ctggacctgc ttgcgttagt ggtgggctgg 120
gaaaaggaag atgagcatgt gattcagttt gtagcaggag aggaggacct taagtttcag 180
cacagcaact tcagggggag agcctcgctg ccaaaggacc agcttttgaa gggaaatgct 240
gcccttcaga tcacagacgt caagctgcag gacgcaggcg tttacaggtg cttaatcagc 300
tacggtggtg cggactacaa gcgaatcacg ctgaaagtca atgcc 345

<210> SEQ ID NO 15
<211> LENGTH: 345
<212> TYPE: DNA
<213> ORGANISM: Artificial Sequence
<220> FEATURE:
<223> OTHER INFORMATION: clone 291 encoding

<400> SEQUENCE: 15
gcgtttacta tcacggctcc aaaggacttg tacgtggtgg agtatggcag caacgtcacg 60
atggagtgca gattccctgt agaacgggag ctggacctgc ttgcgttagt ggtggcctgg 120
gaaaaggaag atgagcacgt gattcagttt gtggcaggag aggaggacct taagcatcag 180
cacagcaact tcagggggag agcctcgctg ccaaaggacc agcttttgaa gggaaatgct 240
gcccttcaga tcacagacgt caagctgcag gacgcaggcg tttaccgctg cataatcagc 300
tacggtggtg cggactacaa gcgaatcacg ctgaaagtca atgcc 345

<210> SEQ ID NO 16
<211> LENGTH: 115
<212> TYPE: PRT
<213> ORGANISM: Artificial Sequence
<220> FEATURE:
<223> OTHER INFORMATION: clone 214

<400> SEQUENCE: 16

Ala Phe Thr Ile Thr Ala Pro Lys Asp Leu Tyr Val Val Glu Tyr Gly
1 5 10 15

```
Ser Asn Val Thr Met Glu Cys Arg Phe Pro Val Glu Arg Glu Leu Asp
            20                  25                  30

Leu Leu Ala Leu Leu Val Asp Trp Glu Lys Glu Asp Glu Gln Val Ile
        35                  40                  45

Arg Phe Glu Ser Gly Glu Glu Asp Leu Lys His Gln His Ser Asn Phe
    50                  55                  60

Arg Gly Arg Ala Ser Leu Pro Lys Asp Gln Leu Leu Lys Gly Asn Ala
65                  70                  75                  80

Ala Leu Gln Ile Thr Asp Val Lys Leu Gln Asp Ala Gly Val Tyr Arg
                85                  90                  95

Cys Ile Ile Ser Tyr Gly Gly Ala Asp Tyr Lys Arg Ile Thr Leu Lys
            100                 105                 110

Val Asn Ala
        115


<210> SEQ ID NO 17
<211> LENGTH: 115
<212> TYPE: PRT
<213> ORGANISM: Artificial Sequence
<220> FEATURE:
<223> OTHER INFORMATION: clone 258

<400> SEQUENCE: 17

Ala Phe Thr Ile Thr Ala Pro Lys Asp Leu Tyr Val Val Glu Tyr Gly
1               5                   10                  15

Ser Asn Val Thr Met Glu Cys Arg Phe Pro Val Glu Arg Glu Leu Asp
            20                  25                  30

Leu Leu Ala Leu Val Val Ser Trp Glu Lys Glu Asp Glu Gln Val Ile
        35                  40                  45

Gln Phe Val Ala Gly Glu Glu Asp Leu Lys Phe Gln His Ser Asn Phe
    50                  55                  60

Arg Gly Arg Ala Ser Leu Pro Lys Asp Gln Leu Leu Lys Gly Asn Ala
65                  70                  75                  80

Ala Leu Gln Ile Thr Asp Val Lys Leu Gln Asp Ala Gly Val Tyr Arg
                85                  90                  95

Cys Leu Ile Ser Tyr Gly Gly Ala Asp Tyr Lys Arg Ile Thr Leu Lys
            100                 105                 110

Val Asn Ala
        115


<210> SEQ ID NO 18
<211> LENGTH: 115
<212> TYPE: PRT
<213> ORGANISM: Artificial Sequence
<220> FEATURE:
<223> OTHER INFORMATION: clone 243

<400> SEQUENCE: 18

Ala Phe Thr Ile Thr Ala Pro Lys Asp Leu Tyr Val Val Glu Tyr Gly
1               5                   10                  15

Ser Asn Val Thr Met Glu Cys Arg Phe Pro Val Glu Arg Glu Leu Asp
            20                  25                  30

Leu Leu Ala Leu Val Val Ala Trp Glu Lys Glu Asp Glu His Val Ile
        35                  40                  45

Gln Phe Val Thr Gly Glu Glu Asp Leu Lys Phe Gln His Ser Asn Phe
    50                  55                  60
```

```
Arg Gly Arg Ala Ser Leu Pro Lys Asp Gln Leu Leu Lys Gly Asn Ala
65                  70                  75                  80

Ala Leu Gln Ile Thr Asp Val Lys Leu Gln Asp Ala Gly Val Tyr Arg
                85                  90                  95

Cys Ile Ile Ser Tyr Gly Gly Ala Asp Tyr Lys Arg Ile Thr Leu Lys
            100                 105                 110

Val Asn Ala
        115


<210> SEQ ID NO 19
<211> LENGTH: 115
<212> TYPE: PRT
<213> ORGANISM: Artificial Sequence
<220> FEATURE:
<223> OTHER INFORMATION: clone 246

<400> SEQUENCE: 19

Ala Phe Thr Ile Thr Ala Pro Lys Asp Leu Tyr Val Val Glu Tyr Gly
1               5                   10                  15

Ser Asn Val Thr Met Glu Cys Arg Phe Pro Val Glu Arg Glu Leu Asp
            20                  25                  30

Leu Leu Ala Leu Val Val Gly Trp Glu Lys Glu Asp Glu His Val Ile
        35                  40                  45

Gln Phe Val Ala Gly Glu Glu Asp Leu Lys Phe Gln His Ser Asn Phe
    50                  55                  60

Arg Gly Arg Ala Ser Leu Pro Lys Asp Gln Leu Leu Lys Gly Asn Ala
65                  70                  75                  80

Ala Leu Gln Ile Thr Asp Val Lys Leu Gln Asp Ala Gly Val Tyr Arg
                85                  90                  95

Cys Leu Ile Ser Tyr Gly Gly Ala Asp Tyr Lys Arg Ile Thr Leu Lys
            100                 105                 110

Val Asn Ala
        115


<210> SEQ ID NO 20
<211> LENGTH: 115
<212> TYPE: PRT
<213> ORGANISM: Artificial Sequence
<220> FEATURE:
<223> OTHER INFORMATION: clone 291

<400> SEQUENCE: 20

Ala Phe Thr Ile Thr Ala Pro Lys Asp Leu Tyr Val Val Glu Tyr Gly
1               5                   10                  15

Ser Asn Val Thr Met Glu Cys Arg Phe Pro Val Glu Arg Glu Leu Asp
            20                  25                  30

Leu Leu Ala Leu Val Val Ala Trp Glu Lys Glu Asp Glu His Val Ile
        35                  40                  45

Gln Phe Val Ala Gly Glu Glu Asp Leu Lys His Gln His Ser Asn Phe
    50                  55                  60

Arg Gly Arg Ala Ser Leu Pro Lys Asp Gln Leu Leu Lys Gly Asn Ala
65                  70                  75                  80

Ala Leu Gln Ile Thr Asp Val Lys Leu Gln Asp Ala Gly Val Tyr Arg
                85                  90                  95
```

```
Cys Ile Ile Ser Tyr Gly Gly Ala Asp Tyr Lys Arg Ile Thr Leu Lys
            100                 105                 110

Val Asn Ala
        115


<210> SEQ ID NO 21
<211> LENGTH: 366
<212> TYPE: PRT
<213> ORGANISM: Artificial Sequence
<220> FEATURE:
<223> OTHER INFORMATION: 214-Fc

<400> SEQUENCE: 21

Met Tyr Arg Met Gln Leu Leu Ser Cys Ile Ala Leu Ser Leu Ala Leu
1               5                   10                  15

Val Thr Asn Ser Ala Phe Thr Ile Thr Ala Pro Lys Asp Leu Tyr Val
            20                  25                  30

Val Glu Tyr Gly Ser Asn Val Thr Met Glu Cys Arg Phe Pro Val Glu
        35                  40                  45

Arg Glu Leu Asp Leu Leu Ala Leu Leu Val Asp Trp Glu Lys Glu Asp
    50                  55                  60

Glu Gln Val Ile Arg Phe Glu Ser Gly Glu Glu Asp Leu Lys His Gln
65                  70                  75                  80

His Ser Asn Phe Arg Gly Arg Ala Ser Leu Pro Lys Asp Gln Leu Leu
                85                  90                  95

Lys Gly Asn Ala Ala Leu Gln Ile Thr Asp Val Lys Leu Gln Asp Ala
            100                 105                 110

Gly Val Tyr Arg Cys Ile Ile Ser Tyr Gly Gly Ala Asp Tyr Lys Arg
        115                 120                 125

Ile Thr Leu Lys Val Asn Ala Gly Ser Arg Ser Asp Lys Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335
```

```
Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365


<210> SEQ ID NO 22
<211> LENGTH: 366
<212> TYPE: PRT
<213> ORGANISM: Artificial Sequence
<220> FEATURE:
<223> OTHER INFORMATION: 258-Fc

<400> SEQUENCE: 22

Met Tyr Arg Met Gln Leu Leu Ser Cys Ile Ala Leu Ser Leu Ala Leu
1               5                   10                  15

Val Thr Asn Ser Ala Phe Thr Ile Thr Ala Pro Lys Asp Leu Tyr Val
            20                  25                  30

Val Glu Tyr Gly Ser Asn Val Thr Met Glu Cys Arg Phe Pro Val Glu
        35                  40                  45

Arg Glu Leu Asp Leu Leu Ala Leu Val Val Ser Trp Glu Lys Glu Asp
    50                  55                  60

Glu Gln Val Ile Gln Phe Val Ala Gly Glu Glu Asp Leu Lys Phe Gln
65                  70                  75                  80

His Ser Asn Phe Arg Gly Arg Ala Ser Leu Pro Lys Asp Gln Leu Leu
                85                  90                  95

Lys Gly Asn Ala Ala Leu Gln Ile Thr Asp Val Lys Leu Gln Asp Ala
            100                 105                 110

Gly Val Tyr Arg Cys Leu Ile Ser Tyr Gly Gly Ala Asp Tyr Lys Arg
        115                 120                 125

Ile Thr Leu Lys Val Asn Ala Gly Ser Arg Ser Asp Lys Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335
```

Gln Gln Gly Asn Val Phe Ser Cys Ser Val Met His Glu Ala Leu His
340 345 350

Asn His Tyr Thr Gln Lys Ser Leu Ser Leu Ser Pro Gly Lys
355 360 365

<210> SEQ ID NO 23
<211> LENGTH: 1098
<212> TYPE: DNA
<213> ORGANISM: Artificial Sequence
<220> FEATURE:
<223> OTHER INFORMATION: 214-Fc encoding

<400> SEQUENCE: 23
atgtacagga tgcaactcct gtcttgcatt gcactaagtc ttgcacttgt cacgaattcg 60
gcgtttacta tcacggctcc aaaggacttg tacgtggtgg agtatggcag caacgtcacg 120
atggagtgca gattccctgt agaacgggag ctggacctgc ttgcgttatt ggtggactgg 180
gaaaaggaag atgagcaagt gattcgattt gagtcaggag aggaggacct taagcatcag 240
cacagcaact tcagggggag agcctcgctg ccaaaggacc agcttttgaa gggaaatgct 300
gcccttcaga tcacagacgt caagctgcag gacgcaggcg tttaccgctg cataatcagc 360
tacggtggtg cggactacaa gcgaatcacg ctgaaagtca atgccggcag cagatctgac 420
aaaactcaca catgcccacc gtgcccagca cctgaactcc tggggggacc gtcagtcttc 480
ctcttccccc caaaacccaa ggacaccctc atgatctccc ggacccctga ggtcacatgc 540
gtggtggtgg acgtgagcca cgaagaccct gaggtcaagt tcaactggta cgtggacggc 600
gtggaggtgc ataatgccaa gacaaagccg cgggaggagc agtacaacag cacgtaccgt 660
gtggtcagcg tcctcaccgt cctgcaccag gactggctga atggcaagga gtacaagtgc 720
aaggtctcca acaaagccct cccagccccc atcgagaaaa ccatctccaa agccaaaggg 780
cagccccgag aaccacaggt gtacaccctg cccccatccc gggaggagat gaccaagaac 840
caggtcagcc tgacctgcct ggtcaaaggc ttctatccca gcgacatcgc cgtggagtgg 900
gagagcaatg ggcagccgga gaacaactac aagaccacgc ctcccgtgct ggactccgac 960
ggctccttct tcctctacag caagctcacc gtggacaaga gcaggtggca gcaggggaac 1020
gtcttctcat gctccgtgat gcatgaggct ctgcacaacc actacacgca gaagagcctc 1080
tccctgtctc cgggtaaa 1098

<210> SEQ ID NO 24
<211> LENGTH: 1098
<212> TYPE: DNA
<213> ORGANISM: Artificial Sequence
<220> FEATURE:
<223> OTHER INFORMATION: 258-Fc encoding

<400> SEQUENCE: 24
atgtacagga tgcaactcct gtcttgcatt gcactaagtc ttgcacttgt cacgaattcg 60
gcgtttacta tcacggctcc aaaggacttg tacgtggtgg agtatggcag caacgtcacg 120
atggagtgca gattccctgt agaacgggag ctggacctgc ttgcgttagt agtgtcctgg 180
gaaaaggaag atgagcaagt gattcagttt gtggccggag aggaggacct taagtttcag 240
cacagcaact tcagggggag agcctcgctg ccaaaggacc agcttttgaa gggaaatgct 300
gcccttcaga tcacagacgt caagctgcag gacgcaggcg tttacaggtg cctaatcagc 360
tacggtggtg cggactacaa gcgaatcacg ctgaaagtca atgccggcag cagatctgac 420

```
aaaactcaca catgcccacc gtgcccagca cctgaactcc tgggggggacc gtcagtcttc    480

ctcttccccc caaaacccaa ggacaccctc atgatctccc ggacccctga ggtcacatgc    540

gtggtggtgg acgtgagcca cgaagaccct gaggtcaagt tcaactggta cgtggacggc    600

gtggaggtgc ataatgccaa gacaaagccg cgggaggagc agtacaacag cacgtaccgt    660

gtggtcagcg tcctcaccgt cctgcaccag gactggctga atggcaagga gtacaagtgc    720

aaggtctcca acaaagccct cccagccccc atcgagaaaa ccatctccaa agccaaaggg    780

cagccccgag aaccacaggt gtacaccctg cccccatccc gggaggagat gaccaagaac    840

caggtcagcc tgacctgcct ggtcaaaggc ttctatccca gcgacatcgc cgtggagtgg    900

gagagcaatg ggcagccgga gaacaactac aagaccacgc ctcccgtgct ggactccgac    960

ggctccttct tcctctacag caagctcacc gtggacaaga gcaggtggca gcaggggaac   1020

gtcttctcat gctccgtgat gcatgaggct ctgcacaacc actacacgca gaagagcctc   1080

tccctgtctc cgggtaaa                                                  1098
```

<210> SEQ ID NO 25
<211> LENGTH: 4
<212> TYPE: PRT
<213> ORGANISM: Artificial Sequence
<220> FEATURE:
<223> OTHER INFORMATION: GSRS linker

<400> SEQUENCE: 25

```
Gly Ser Arg Ser
1
```

<210> SEQ ID NO 26
<211> LENGTH: 290
<212> TYPE: PRT
<213> ORGANISM: Homo sapiens

<400> SEQUENCE: 26

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175
```

-continued

```
Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

PD-L1 VARIANTS WITH IMPROVED AFFINITY TOWARDS PD-1

The present invention relates to a PD-L1 polypeptide comprising at least a first amino acid sequence at least 70% identical to SEQ ID NO:8, and at least a second sequence at least 70% identical to SEQ ID NO:10, wherein the polypeptide carries amino acid substitutions at least at the amino acid positions Y56 and P76, wherein the amino acid positions are based on the murine PD-L1 amino acid sequence (SEQ ID NO:6). The present invention also relates to a polynucleotide encoding the aforesaid PD-L1 polypeptide, and to host cells, methods, and uses related thereto.

Sepsis is a life-threatening illness that can occur when the whole body reacts to an infection. Despite intensive research, sepsis remains the third leading cause of mortality in intensive care units. Pathophysiologically, during sepsis progression there is an initial hyper-inflammatory phase which provokes the onset of a hypo-inflammatory stage, partly occurring in parallel (Vincent, et al. (2013) Lancet 381:774-775).

Recent therapy approaches mainly focus on the treatment of the hyper-inflammatory response to confine the release of pro-inflammatory mediators, block their function, or remove them from the circulation. One most promising candidate, inhibition of which was shown to significantly improve sepsis survival in a rodent model, was TNFα. Using neutralizing antibodies, this approach was translated into the human situation, but failed to improve sepsis survival (Reinhart et al. (2001) Crit Care Med 29:765-769). By blocking immune stimulation, the hyper-inflammation is limited and most patients survive this phase; however, because blocking the pro-inflammatory immune response reduces the host's ability to fight and control primary and secondary infections, this therapy approach finally failed to significantly improve sepsis survival, but caused or enhanced the hypo-inflammatory phase. This immunosuppression often provokes multi-organ-dysfunction syndrome (MODS) and the patient's death (Otto et al. (2011) Crit Care 15:R183). In a different approach, Fc-fusion proteins of the extracellular portion of the human PD-L1 polypeptide were provided for treatment and prevention of organ failure during sepsis (WO 2017/029389 A1).

Treatment approaches to rescue the patient during immune paralysis have also been applied. Taking into consideration that monocytes are deactivated, GM-CSF treatment restored monocyte function during sepsis (Meisel et al. (2009) Am J Respir Crit Care Med 180:640-648). Nonetheless. due to the multi causal origin of sepsis, the various pre-existing co-morbidities, or genetic preconditions of the patients, an appropriate patient specific treatment is still difficult to achieve (Hotchkiss and Opal (2010) *N Engl J Med* 363:87-89).

In general, disease severity is already far advanced when sepsis is diagnosed in patients and liver damage, a relatively late event during sepsis progression, has already occurred. During sepsis, organ failure, often followed by a multi-organ-dysfunction syndrome (MODS), frequently results in the patient's death. Therefore, understanding mechanisms leading to organ damage are mandatory to improve already existing care options or to set up new therapy approaches.

A process that results in organ damage in sepsis is an unwanted autoimmune activation of cytotoxic T-cells (CTLs) mounting attacks on host cells. The activation of cytotoxic T-cells is a tightly regulated process and requires multiple signaling events to occur simultaneously. In a healthy situation, binding events at the immune synapse such as T-cell receptors (TCRs) binding to major-histocompatibility complex 1 (MHC-1) or programmed cell death-1 (PD-1) binding to PD-1 ligand 1 (PD-L1) on epithelial cells regulate the activation of CTLs. However, during an infection causing an inflammatory response by CTLs, epithelial cells undergo several changes. For example, the presentation of non-self peptides on MHC-I proteins on an infected cell activates CTLs, which causes the rapid destruction of the infected tissue. Another example for the activation of CTLs is the absence of PD-L1 on the surface of host cells, which is caused amongst other factors by the presence of bacterial toxins in their environment. Via the recognition of Toll-like receptors, these bacterial toxins induce the expression of phagocyte NADPH oxidase (NOX2), resulting in an increase of reactive oxygen species (ROS) levels in the cytosol and the removal of PD-L1 from the cell surface (von Knethen et al. (2019), Theranostics 9(7):2003). While both these processes are essential to remove diseased cells during normal infection, in particular the loss of PD-L1 becomes problematic during massive infection of large organs, or bacterial infection of large section of body tissue. Then the organs are attacked by the patient's own immune response without being infected, causing permanent injury or, in the worst case, organ failure and death.

Thus, there is a strong need for improved means and methods for the modulation of PD-1 signaling, in particular on the surface of CTLs, e.g. in particular for treatment and/or prevention of organ failure during sepsis.

The technical problem underlying the present invention can be seen as the provision of means and methods for complying with the aforementioned needs. The technical problem is solved by the embodiments characterized in the claims and embodiments herein below.

Therefore, the present invention relates to a PD-L1 polypeptide comprising at least a first amino acid sequence at least 70% identical to SEQ ID NO:8, and at least a second sequence at least 70% identical to SEQ ID NO:10, wherein (I) the polypeptide carries an amino acid substitution at least at one of the following positions: V54, Y56, Q63, Q66, V68, A69, P76, I115, A121, D122, Y123, K124, and R125, wherein, if the polypeptide comprises an amino acid substitution at position Y56, C113 or I115, the polypeptide carries at least one further of the aforesaid substitutions; wherein the amino acid positions are based on the murine PD-L1 amino acid sequence (SEQ ID NO 6);

(II) the polypeptide carries amino acid substitutions at least at the amino acid positions Y56 and P76, wherein the amino acid positions are based on the murine PD-L1 amino acid sequence (SEQ ID NO:6); and/or (III) wherein the polypeptide carries at least one amino acid substitution in at least one of the following amino acid positions within the first amino acid sequence: V54, Y56, Q63, Q66, V68, A69, P76; and at least one amino acid substitution in at least one of the following amino acid positions within the second amino acid sequence: I115, A121, D122, Y123, K124, and R125, wherein the amino acid positions are based on the murine PD-L1 amino acid sequence (SEQ ID NO:6).

In general, terms used herein are to be given their ordinary and customary meaning to a person of ordinary skill in the art and, unless indicated otherwise, are not to be limited to a special or customized meaning. As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements. Also, as is understood by the skilled person, the expressions "comprising a" and "comprising an" preferably refer to "comprising one or more", i.e. are equivalent to "comprising at least one".

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

As used herein, the term "standard conditions", if not otherwise noted, relates to IUPAC standard ambient temperature and pressure (SATP) conditions, i.e. preferably, a temperature of 25° C. and an absolute pressure of 100 kPa; also preferably, standard conditions include a pH of 7. Moreover, if not otherwise indicated, the term "about" relates to the indicated value with the commonly accepted technical precision in the relevant field, preferably relates to the indicated value±20%, more preferably ±10%, most preferably ±5%. Further, the term "essentially" indicates that deviations having influence on the indicated result or use are absent, i.e. potential deviations do not cause the indicated result to deviate by more than ±20%, more preferably ±10%, most preferably ±5%. Thus, "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Preferably, a composition consisting essentially of a set of components will comprise less than 5% by weight, more preferably less than 3% by weight, even more preferably less than 1% by weight, most preferably less than 0.1% by weight of non-specified component(s).

The degree of identity (e.g. expressed as "% identity") between two biological sequences, preferably DNA, RNA, or amino acid sequences, can be determined by algorithms well known in the art. Preferably, the degree of identity is determined by comparing two optimally aligned sequences over a comparison window, where the fragment of sequence in the comparison window may comprise additions or deletions (e.g., gaps or overhangs) as compared to the sequence it is compared to for optimal alignment. The percentage is calculated by determining, preferably over the whole length of the polynucleotide or polypeptide, the number of positions at which the identical residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. In the context of biological sequences referred to herein, the term "essentially identical" indicates a % identity value of at least 80%, preferably at least 90%, more preferably at least 98%, most preferably at least 99%. As will be understood, the term essentially identical includes 100% identity. The aforesaid applies to the term "essentially complementary" mutatis mutandis.

The term "fragment" of a biological macromolecule, preferably of a polynucleotide or polypeptide, is used herein in a wide sense relating to any sub-part, preferably subdomain, of the respective biological macromolecule comprising the indicated sequence, structure and/or function. Thus, the term includes sub-parts generated by actual fragmentation of a biological macromolecule, but also sub-parts derived from the respective biological macromolecule in an abstract manner, e.g. in silico. Thus, as used herein, an Fc or Fab fragment, but also e.g. a single-chain antibody, a bispecific antibody, and a nanobody may be referred to as fragments of an immunoglobulin.

Unless specifically indicated otherwise herein, the compounds specified, in particular the PD-L1 polypeptides, may be comprised in larger structures, e.g. may be covalently or non-covalently linked to carrier molecules, retardants, and other excipients. In particular, polypeptides as specified may be comprised in fusion polypeptides comprising further peptides, which may serve e.g. as a tag for purification and/or detection, as a linker, or to extend the in vivo half-life of a compound. The term "detectable tag" refers to a stretch of amino acids which are added to or introduced into the fusion polypeptide; preferably, the tag is added C- or N-terminally to the fusion polypeptide of the present invention. Said stretch of amino acids preferably allows for detection of the fusion polypeptide by an antibody which specifically recognizes the tag; or it preferably allows for forming a functional conformation, such as a chelator; or it preferably allows for visualization, e.g. in the case of fluorescent tags. Preferred detectable tags are the Myc-tag, FLAG-tag, 6-His-tag, HA-tag, GST-tag or a fluorescent protein tag, e.g. a GFP-tag. These tags are all well known in the art. Other further peptides preferably comprised in a fusion polypeptide comprise further amino acids or other modifications which may serve as mediators of secretion, as mediators of blood-brain-barrier passage, as cell-penetrating peptides, and/or as immune stimulants. Further polypeptides or peptides to which the polypeptides may be fused are signal and/or transport sequences, e.g. an IL-2 signal sequence, linker sequences, e.g. a GSRS (SEQ ID NO:25) peptide linker, The term "polypeptide", as used herein, refers to a molecule consisting of several, typically at least 20 amino acids that are covalently linked to each other by peptide bonds. Molecules consisting of less than 20 amino acids covalently linked by peptide bonds are usually considered to be "peptides". Preferably, the polypeptide comprises of from 50 to 1000, more preferably of from 75 to 1000, still more preferably of from 100 to 500, most preferably of from 110 to 400 amino acids. Preferably, the polypeptide is comprised in a fusion polypeptide and/or a polypeptide complex.

A "fusion polypeptide" in accordance with the present description refers to a polypeptide that is composed of at least two polypeptides or peptides, comprised in a continuous chain of peptide bonds. Thus, the fusion polypeptide preferably is expressible in vivo from a single expression construct, more preferably from a single open reading frame. Preferably, the fusion protein comprises at least a PD-L1 polypeptide and at least one further peptide or polypeptide, preferably a polypeptide extending the in vivo half-life of a fusion polypeptide it is comprised in; suitable polypeptides are described elsewhere herein. The fusion polypeptide may, however, comprise two, three, four, five or even more additional polypeptide or peptide portions, e.g. a signal sequence, a linker, a hinge region, and/or polypeptide extending the in vivo half-life. The fusion polypeptide may be expressed in vivo from a polynucleotide encoding the fusion polypeptide, which may be synthesized e.g. chemically or by recombinant DNA techniques, and expressed in a suitable expression system. Thereafter, the expressed fusion polypeptide can be purified from the expression system.

The term "polypeptide complex", as used herein, relates to any compound comprising at least two polypeptides and/or peptides not connected via a peptide bond. Thus, the polypeptides and/or peptides in the fusion polypeptide may be linked via a covalent bond, in particular a disulfide bond, or non-covalently, in particular via ionic bonds, hydrogen bonds and/or van der Waals forces, e.g. in an affinity binding. Various affinity binding systems comprising a ligand and a receptor portion are known to the skilled artisan, enabling construction of affinity pairs of polypeptides comprising the different peptide or polypeptide portions reversibly bound to each other without further ado. Typical examples of such affinity binding systems are those based on antibodies/antigens, streptavidin/biotin, avidin/biotin, and others well known in the art. Preferably, the polypeptide complex comprises at least a PD-L1 polypeptide and at least one further peptide or polypeptide, preferably a polypeptide extending the in vivo half-life of a fusion polypeptide it is comprised in; suitable polypeptides are described elsewhere herein.

The term "PD-L1 polypeptide", as used herein, relates to a polypeptide comprising at least a first amino acid sequence at least 70% identical to SEQ ID NO:8, and at least a second sequence at least 70% identical to SEQ ID NO:10; furthermore, the PD-L1 polypeptide comprises at least one of the amino acid substitutions or combinations of amino acid substitutions compared to the sequence of SEQ ID NO:6 indicated above. As the skilled person understands, the term "substitution" in the context of amino acid sequences relates to a replacement of an amino acid by a non-identical amino acid. As the skilled person will understand, the underlying structure of the PD-L1 polypeptide referred to herein is preferably derived from the known structure of PD-L1 proteins, preferably the human PD-L1 protein (Genbank Acc No: NP_054862.1, SEQ ID NO:26) and/or the mouse PD-L1 protein (Genbank Acc No: ADK70950.1, SEQ ID NO:6, preferably encoded by the sequence of SEQ ID NO:3). In accordance, all indications of amino acid positions within the PD-L1 polypeptide are provided relative to the amino acid sequence of mouse PD-L1 as specified above (SEQ ID NO:6). As the skilled person will also understand, a corresponding position in an PD-L1 polypeptide having more or less amino acids is preferably determined by aligning the PD-L1 polypeptide with SEQ ID NO:6, preferably as specified herein above. The PD-L1 polypeptide has the biological activity of binding PD-1, preferably human PD-1 (Genbank Acc No: NP_005009.2) and/or mouse PD-1 (Genbank Acc No: NP_032824.1). Preferably, the PD-L1 polypeptide has the biological activity of binding a recombinant fragment of murine PD-1 comprising amino acids 31-150 of the complete protein. Preferably, the Kd of the binding between the PD-L1 polypeptide and PD-1, preferably the aforesaid recombinant fragment of murine PD-L1, is at most 50 nM, more preferably, at most 20 nM, still more preferably at most 10 nM, even more preferably at most 7.5 nM, even more preferably at most 5 nM, most preferably at most 2.5 nM. As disclosed in more detail herein in the Examples, presence of a further polypeptide, e.g. in a fusion polypeptide, may influence the affinity of the PD-L1 polypeptide; thus, the aforesaid Kd values are preferably determined for a peptide corresponding to amino acids 18 to 132 of wildtype PD-L1, preferably to SEQ ID NO:4. Preferably, the PD-L1 polypeptide further has the activity of inhibiting sepsis-induced cytotoxic T-cells; Also preferably, the PD-L1 polypeptide further has the activity of inducing a long-lasting tolerance in cytotoxic T-cells in the subject against sepsis-caused activation. In a preferred embodiment, the PD-L1 polypeptide has the activity of reducing, more preferably preventing, IFN-γ and/or TNF-α secretion by white blood cells, preferably T cells. In a preferred embodiment, the PD-L1 polypeptide has the activity of reducing, more preferably preventing, IFN-γ secretion by T cells, preferably CD4+ and/or CD8+ T cells; and/or TNF-α secretion by macrophages. In a further preferred embodiment, the PD-L1 polypeptide is a PD-1 agonist, preferably a PD-1 agonist with increased affinity to PD-1 compared to wildtype PD-L1.

The PD-L1 polypeptide comprises at least the first amino acid sequence and the second amino acid sequence as specified above. Preferably, the first amino acid sequence is at least 80%, preferably at least 90%, more preferably at least 95% identical to SEQ ID NO:8 and/or the second amino acid sequence is at least 80%, preferably at least 90%, more preferably at least 95% identical to SEQ ID NO:10. Most preferably, the PD-L1 polypeptide comprises at least a first amino acid sequence selected from SEQ ID NO:7 and SEQ ID NO:8, and at least a second sequence selected from SEQ ID NO:9 and SEQ ID NO:10, including the amino acid substitution or substitutions as specified herein. As will be understood, the aforesaid first and second amino acid sequence are derivable from the human and/or the mouse PD-L1 protein. Thus, the PD-L1 polypeptide preferably comprises further sequences derivable from said PD-L1 protein(s), in particular a sequence at least 70% identical to the sequence connecting the aforesaid first and second amino acid sequence in human and/or the mouse PD-L1 protein, i.e. an amino acid sequence at least 70% identical to amino acids 77 to 112 of human PD-L1 protein. It is, however, also envisaged that the first and second amino acid sequence are connected via a sequence not derivable from a PD-L1 protein, e.g. a suitable linker peptide. Nonetheless, preferably, the PD-L1 polypeptide comprises, preferably consists of, an amino acid sequence at least 70% identical to amino acids 18 to 132 of human PD-L1, i.e. the amino acid sequence of SEQ ID NO:5. Preferably, the PD-L1 polypeptide comprises, preferably consists of, an amino acid sequence at least 80%, preferably at least 90%, more preferably at least 95% identical to the amino acid sequence of SEQ ID NO:5. More preferably, the PD-L1 polypeptide comprises, preferably consists of, the amino acid sequence of SEQ ID NO:4 or SEQ ID NO:5, including the substitution(s) as specified elsewhere herein. As will be understood, the expression "the PD-L1 polypeptide comprises the amino acid sequence X, including the substitution(s) as specified elsewhere herein" relates to the fact that the PD-L1 polypeptide comprises essentially the amino acid sequence X, but includes the indicated substitutions; i.e. preferably, the PD-L1 polypeptide comprises the amino acid sequence X except that the amino acid(s) at the indicated position(s) is/are replaced by the substituting amino acid(s).

The PD-L1 polypeptide as specified herein carries an amino acid substitution at least at one of the following positions: V54, Y56, Q63, Q66, V68, A69, P76, I115, A121, D122, Y123, K124, and R125, wherein, if the polypeptide comprises an amino acid substitution at position Y56, C113, or I115, the polypeptide carries at least one further of the aforesaid substitutions, i.e. selected from substitutions from the list consisting of V54, Y56, Q63, Q66, V68, A69, P76, I115, A121, D122, Y123, K124, and R125. More preferably, if the polypeptide comprises an amino acid substitution at position Y56, Q63, A69, P76, C113, or I115, the polypeptide carries at least one further of the aforesaid substitutions. More preferably, the PD-L1 polypeptide comprises at least one amino acid substitution at position Y56 and/or P76, more preferably at position Y56 and P76. Also preferably, the PD-L1 polypeptide carries at least one further substitution at at least one of the amino acid positions V54, Q66, V68, A69 and/or I115. More preferably, the PD-L1 polypeptide carries at least one amino acid substitution in at least one of the following amino acid positions within the first amino acid sequence: V54, Y56, Q63, Q66, V68, A69, P76; and at least one amino acid substitution in at least one of the following amino acid positions within the second amino acid sequence: I115, A121, D122, Y123, K124, and R125. Preferably, the Q63 substitution is not a Q63N substitution, the A69 substitution is not a A69H substitution, the P76 substitution is not a P76V substitution, and/or the I115 substitution is not a I115M substitution. More preferably, the V54 substitution is a V54L substitution, the Y56 substitution is a Y56G, Y56A, Y56D, or Y56S substitution, the Q63 substitution is a Q63H substitution, the Q66 substitution is a Q66R substitution, the V68 substitution is a V68E substitution, the A69 substitution is a A69T or A69S substitution, the P76 substitution is a P76F or P76H substitution, and/or the I115 substitution is a I115L. Preferably, the PD-L1 polypeptide carries at least a further substitution at the amino acid position C113. Also preferably, the PD-L1 polypeptide carries at least one further substitution at at least one of the amino acid positions V54, Q66, V68, A69 and/or I115.

Preferably, the PD-L1 polypeptide comprises the substitutions (i) Y56S, P76F, and I115L; (ii) V54L, Y56D, Q66R, V68E, A69S, and P76H; (iii)Y56G, Q63H, P76F, and I15L; (iv) Y56A, Q63H, A69T, and P76F; or (v) Y56A, Q63H, and P76H. Most preferably, the PD-L1 polypeptide comprises the substitutions Y56S, P76F, and I115L; or V54L, Y56D, Q66R, V68E, A69S, and P76H. Thus, preferably, the PD-L1 polypeptide comprises, preferably consists of, any of the amino acid sequences as shown in SEQ ID NO:16 to SEQ ID NO:20; preferably wherein the PD-L1 polypeptide comprises, preferably consists of, the amino acid sequence as shown SEQ ID NO:16 or SEQ ID NO:17.

Preferably, the PD-L1 polypeptide is comprised in a fusion polypeptide and or a polypeptide complex, as also specified herein above. Preferably, the PD-L1 polypeptide is comprised in a fusion polypeptide further comprising a tag for purification and/or detection, a linker, and/or a polypeptide extending the in vivo half-life of a compound. Polypeptides extending the in vivo half-life of a compound are known in the art and include in particular an antibody fragment, e.g. an Fc fragment of an immunoglobulin, and an ovalbumin or fragment thereof. Also preferably, the PD-L1 polypeptide is comprised in a polypeptide complex; e.g. the aforesaid tag for purification and/or detection, linker, and/or polypeptide extending the in vivo half-life of a compound may be connected to the PD-L1 polypeptide via a disulfide bond or via affinity binding as specified elsewhere herein. Also, a fusion polypeptide may form multimers, e.g. dimers, in which case the PD-L1 polypeptide may be comprised in a fusion polypeptide and in a polypeptide complex, such as in a dimeric Fc fusion polypeptide. Thus, preferably, the PD-L1 polypeptide comprises, preferably consists of, an amino acid sequence as shown in SEQ ID NO:21 or 22, preferably encoded by a polynucleotide comprising the nucleotide sequence of SEQ ID NO:23 or 24.

The term "Fragment crystallizable (Fc) portion of an immunoglobulin" refers to antibody fragments which comprise the $C_H2$ and $C_H3$ domains of an antibody and which can be obtained by proteolytic cleavage of an antibody using, e.g., papain. Various immunoglobulins are known in the art from a variety of different species. These immunoglobulins encompass IgA, IgD, IgE, IgG, IgM, IgW or IgY. Preferred in accordance with the present invention among the immunoglobulins are, however, those which appear in mammals and, in particular, in humans, i.e. IgA, IgD, IgE, IgG, IgM. The Fc portion of an antibody determines the class effect. Since only the constant domains of the heavy chains form the Fc portion of an antibody, the classes of the heavy chains determine the class effects. Possible classes of heavy chains in antibodies encompass alpha, gamma, delta, epsilon, and mu. These heavy chain classes define the isotype. Different isotypes of antibodies have different class effects due to their respective Fc portions. Such Fc mediated class effects include those affecting effector cells or effector molecules, e.g., opsonisation, agglutination, haemolysis, complement activation, and mast cell degranulation. Amino acid sequences for $C_H2$ and $C_H3$ domains forming the Fc portions are well known in the art for different antibody isotypes and can be provided by the skilled artisan without further ado. The Fc portion as referred to in accordance with the present invention may be, preferably, posttranslationally modified and, more preferably, glycosylated. Preferably, said immunoglobulin in accordance with the present invention is IgG and, more preferably, human IgG. Amino acid sequences encoding human IgG are well known in the art as well as the nucleic acid sequences encoding them. Moreover, it is also well known which amino acids correspond to the Fc portions in the said amino acid sequences.

Preferably the said fusion polypeptide or polypeptide complex comprises a third portion for targeting and, in particular, a third portion being a polypeptide capable of binding specifically to cytotoxic T-cells. More preferably, said polypeptide capable of binding specifically to cytotoxic T-cells is selected from the group consisting of a polypeptide comprising a portion of the MHC-I complex which is capable of binding to CD8, a portion of the CD80 which is capable of binding to CD28, a polypeptide being an antibody or fragment thereof capable of specifically binding to CD8, a polypeptide being an antibody or fragment thereof capable of specifically binding to CD28, and CD2-binding portion of lymphocyte function associated antigen-3 (LFA-3). How such portions can be derived from the respective proteins is well known to the person skilled in the art.

Advantageously, it has been found in the studies underlying the present invention that PD-L1 derivatives as described have an increased affinity for the ligand PD-1. Moreover, it was found that significantly smaller molecules may be used. Thus, therapeutic efficacy, in particular in treatment of sepsis-related organ failure, can be achieved at lower concentrations, such that the dose required is reduced. Thus, the variants of PD-L1 preferably replace the missing signal from the host cells and thereby prevent the autoimmune activation of CTLs. The PD-L1 variants preferably harbor mutations that enhance the affinity to PD-1, however maintain the same binding mode as PD-L1 wt. Consequently, the engineered PD-L1 variants preferably have the potential to serve as drugs that can be administered to prevent organ/tissue damage in a patient caused by sepsis.

The definitions made above apply mutatis mutandis to the following. Additional definitions and explanations made further below also apply for all embodiments described in this specification mutatis mutandis.

The present invention also relates to a polynucleotide encoding a PD-L1 polypeptide according to the present invention.

The term "polynucleotide" as used herein refers to single- or double-stranded DNA or RNA molecules. Encompassed by the said term is genomic DNA, cDNA, hnRNA, mRNA as well as all naturally occurring or artificial derivatives of such molecular species, including fragments thereof. The polynucleotide may be, preferably, a linear or circular molecule. Moreover, in addition to the nucleic acid sequences encoding the aforementioned PD-L1 polypeptide, a polynucleotide according to the present invention may comprise additional sequences required for proper transcription and/or translation such as 5'- or 3'-UTR sequences or sequences required for splicing or RNA stability. Preferred polynucleotides encoding the PD-L1 polypeptide according to the present invention are also described elsewhere herein. Preferably, the polynucleotide comprises, preferably consists of, a sequence which is at least 60% identical to the sequence shown in SEQ ID NO:1 or SEQ ID NO:2; preferably, the polynucleotide comprises, preferably consists of, a sequence as shown in any one of SEQ ID NO:11 to 15, more preferably SEQ ID NO:11 or 12.

Preferably, the polynucleotide is comprised in an expression construct allowing for expression of the said polynucleotide in the said subject. The term "expression construct" as used herein refers to a heterologous polynucleotide comprising the aforementioned polynucleotide encoding the PD-L1 polypeptide as well as nucleic acids required for expression of the polynucleotide encoding the fusion polypeptide. Typically, such additional nucleic acids, which preferably are heterologous to the polynucleotide encoding the PD-L1 polypeptide, may be promoter sequences, enhancer sequences and/or transcription termination sequences such as terminators. Moreover, the expression construct may also comprise further nucleic acids required for introducing the expression construct into a host. For example, if expression in host cells is desired, the expression construct may comprise further nucleic acids required for transformation or transfection and for propagation of the introduced expression construct in the host cells.

The present invention also relates to a vector comprising the polynucleotide of the present invention.

A vector as meant herein, preferably, encompasses phage, plasmid, viral or retroviral vectors as well as artificial chromosomes, such as bacterial or yeast artificial chromosomes. The vector encompassing the polynucleotide encoding the PD-L1 polypeptide, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. Moreover, the polynucleotide is usually operatively linked to expression control sequences allowing expression in prokaryotic or eukaryotic host cells or isolated fractions thereof in the said vector. Expression of the polynucleotide comprises transcription of the polynucleotide into a translatable mRNA. Regulatory elements ensuring expression in host cells are well known in the art and are described on an exemplary basis herein above. Possible regulatory elements permitting expression in prokaryotic host cells comprise, e.g., the lac-, trp- or tac-promoter in *E. coli*, and examples for regulatory elements permitting expression in eukaryotic host cells are the AOX1- or the GAL1-promoter in yeast or the CMV, SV40-, RSV-promoter (Rous sarcoma virus), CMV-enhancer, SV40-enhancer or a globin intron in mammalian and other animal cells. Other expression systems envisaged by the invention shall permit expression in insect cells, such as polyhedrin promoter based systems. Moreover, inducible expression control sequences may be used in a vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen) or baculovirus-derived vectors. Preferably, the vector is an expression vector and a gene transfer or targeting vector. Expression vectors derived from viruses such as retroviruses, vaccinia virus, adeno-associated virus, herpes viruses, or bovine papilloma virus, may be used for delivery of the expression constructs according to the invention into targeted cell population, e.g. also in gene therapeutic approaches. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Further, it is envisaged to introduce the expression construct into the genome of a host. In such a case, the expression construct may also comprise nucleic acids that allow for either heterologous or homologous integration of the said expression construct. Thus the expression construct referred to herein may also be a targeting constructs which allows for random or site-directed integration of the targeting construct into genomic DNA. Such target constructs, preferably, comprise DNA of sufficient length for either homologous or heterologous recombination flanking the expression cassette with the polynucleotide encoding the PD-L1 polypeptide. Moreover, the expression construct may also be introduced using integration systems like Cre/LoxP or CRISPR/CAS. In such cases, the expression construct may comprise further nucleic acids allowing for the use of such integration systems. Suitable modifications/additions depend on the envisaged integration system and are well known for those skilled in the art.

The present invention also relates to a PD-L1 polypeptide or a polynucleotide according to the present invention for use as a medicament. The present invention further relates to a PD-L1 polypeptide or a polynucleotide according to the present invention for use in treating and/or preventing organ failure in a subject suffering from sepsis, for use in treating immune disorders, preferably lupus, and/or for use in immuno-oncological treatment.

The term "treating", as used herein, refers to ameliorating or curing a disease or at least one symptom associated therewith. Thus, if there is amelioration or cure of the disease or at least a symptom associated therewith, the treatment shall be deemed to be effective. It will be understood that treating might not be effective in all subjects. However, according to the present invention it is envisaged that treatment will preferably be effective in at least a statistically significant portion of subjects to be treated. It is well known to the skilled artisan how to determine a statistically significant portion of subjects that can be effectively treated. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the finding of effective treatment will be correct for at least 60%, at least 70%, at least 80%, or at least 90% of the subjects of a given cohort or population.

The term "preventing" as used herein refers to avoiding the onset of the disease or at least one symptom associated therewith or to prevent the worsening of the disease or the said at least one symptom. The prevention as referred to herein can be typically achieved either for the period during which a drug is administered. If the administration of the drug is stopped, however, the prevention may not persist for an unlimited time but may remain present for a certain preventive time window after application of the drug. Typically, a preventive time window in accordance with the present invention may be at least 1 day, at least 2 days, at least 3 days, at least 4 days, at least 5 days, at least 6 days, or at least 7 days. However, the preventive time window may also depend on the dosage of a drug as well as the mode of administration or the kind of formulation. For example, if a high dosage is applied, usually longer preventive time windows can be achieved. The same holds true if slow release formulations of a drug are administered or the drug is administered via routes that do not lead to immediate metabolization of a drug in the subject. In such cases, the preventive time window may be increased up to several weeks, months or even years. It will be understood that prevention might not be effective in all subjects. However, according to the present invention it is envisaged that prevention preferably will be effective in at least a statistically significant portion of subjects. It is well known to the skilled artisan how to determine a statistically significant portion of subjects that can be effectively prevented. Whether a portion is statistically significant can be determined without further ado by the person skilled in the art using various well known statistic evaluation tools as discussed above.

Since the PD-L1 polypeptide according to the present invention shall be used for medical treatment, it shall, preferably, be formulated as a medicament. A medicament in the sense of the present invention refers, preferably, to a pharmaceutical composition containing the biologically active PD-L1 polypeptide or an expression construct encoding the same according to the invention as pharmaceutically active compound and one or more other components such as one or more pharmaceutically acceptable carrier(s). The pharmaceutically active compound can be present in liquid or lyophilized form. For example, the pharmaceutically active compound can be present together with glycerol and/or protein stabilizers (e.g., human serum albumin). The medicament is, typically, administered systemically and, preferably, intravenously or intramuscularly. However, depending on the nature of the formulation and the desired therapeutic application, the medicament may be administered by other routes as well. The pharmaceutically active compound is the active ingredient or drug of the medicament, and is preferably administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables. The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pennsylvania. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like. The medicament referred to herein is, preferably, administered at least once, e.g. as a bolus. However, the said medicament may be administered more than one time and, preferably, at least twice, e.g. permanently or periodically after defined time windows.

A therapeutically effective dose refers to an amount of the PD-L1 polypeptide or expression construct encoding the same to be used in medicament which prevents, ameliorates or cures the symptoms accompanying a disease or condition referred to in this specification. Therapeutic efficacy and toxicity of a drug can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The dosage regimen will be determined by the attending physician and by clinical factors. As is well known in the medical arts, dosages for any one patient depends upon many factors, including the patient's size, age, the particular formulation of the medicament to be administered, sex, time and route of administration, general health, and other drugs being administered concurrently. Progress can be monitored by periodic assessment. Dosage recommendations shall be indicated in the prescribers or users instructions in order to anticipate dose adjustments depending on the considered recipient.

The medicament according to the present invention may in a further aspect of the invention comprise drugs in addition to the aforementioned compounds which are added during its formulation. Preferably, the pharmaceutically active compound according to the invention is to be applied together with at least one further drug and, thus, may be formulated together with these other drugs as a medicament. More preferably, said at least one further drug is selected from the group consisting of: antibiotics, vasopressors, steroids, anticoagulants, antithrombotics, proinflammatory cytokines and DAMP inhibitors. Also, it is to be understood that the formulation of a pharmaceutical composition preferably takes place under GMP standardized conditions or the like in order to ensure quality, pharmaceutical security, and effectiveness of the medicament.

The term "organ failure" as used herein refers to any dysfunction of the organ which affects the physiologically expected function of an organ to such an extent that normal homeostasis can neither be maintained nor endogenously compensated. Organ failure may be acute or chronic. Symptoms associated with organ failure depend on the affected organ usually become apparent by a pathological physiology in the subject which can be determined, e.g., by clinical or biochemical parameters. Symptoms of organ failure are also well known in the art and are described in medicinal text books. Preferably, organ failure as referred to herein is multi organ failure. Multi organ failure is characterized by the failure of two or more organs at the same time or sequentially within a short period of time. It can be often observed as a consequence of severe infections or inflammatory reactions such as systemic inflammatory response syndrome (SIRS) or sepsis. Typical organs which fail during SIRS or sepsis are lung, kidney, heart and/or the entire circulation system, the gastrointestinal system, including in particular the liver, as well as the nervous system. Preferably, the multi organ failure referred to herein is caused by autoreactive cytotoxic cells and, more preferably, is CD8 cytotoxic T-cell dependent multi-organ failure. Also preferably, organ failure as referred to herein is liver failure, in particular liver failure in septic subjects.

The term "subject" as used herein refers to any kind of animal encompassing, e.g., mammals, birds, fish or reptiles. Typically, the animal, however, is a mammal such as a mammals used as pets including dogs, cats, horses, or rodents, laboratory animals, e.g., rats, mice or apes, or farming animals such as pigs, cows, goats, or sheep. More preferably, the mammal is a primate and, most preferably, a human. The subject according to the present invention shall preferably be known or suspected to suffer from sepsis or be expected to develop sepsis; thus the subject, preferably shows at least one or more pathological changes such as clinically apparent symptoms or changes of physiological or molecular parameters which are typically associated with sepsis. Preferably, the subject is known or suspected to suffer from an immune disorder, preferably lupus. Also preferably, the subject is known or suspected to be in need of immuno-oncological treatment.

The term "sepsis", as used herein, refers to an inflammatory response affecting the entire organism. Typical symptoms associated with sepsis are well known in the art and described in standard textbooks of medicine. They include a significantly altered body temperature (low temperature or fever), rapid breathing, tachycardia, low blood pressure due to decreased peripheral vascular resistance, mental confusion and edema formation. Biochemical parameters such as coagulation dysfunction or metabolic acidosis are also typical signs of sepsis. Sepsis preferably is caused by severe infection by bacteria, viruses, parasites or fungi. Moreover, there are cofounding factors which influence the onset or outcome of sepsis, such as diabetes or cancer. Preferably, sepsis as referred to herein is characterized by the presence of two or more of the following symptoms in response to an infection: abnormal temperature (preferably, below 36° C. or above 38° C.), abnormal heart rate (preferably, above 90 beats/min), abnormal respiratory rate (preferably, above 20 breathings/min) or blood gas composition (preferably, $CO_2$ less than 4.3 kPa), and abnormal white blood cell number (preferably, less than $4\times10^9$/L or more than $12\times10^9$/L or histological presence of band neutrophils).

The term "immune disorder" is understood by the skilled person to relate to any disorder involving an immune reaction attacking a cell type, tissue and/or organ of the subject in which the immune reaction occurs. The immune disorder preferably is caused or aggravated by an allogenic immune response; thus, the immune disorder preferably involves an immune reaction of a host immune system against a foreign tissue or organ, in particular is organ graft rejection, and/or involves an immune reaction of a foreign immune system against a host tissue or organ, in particular is graft-versus-host disease. Preferably, the immune disorder is caused or aggravated by an autologous immune response, i.e. is an immune disorder; thus, the immune disorder preferably is a disorder in which T-cells, preferably CD8 T-cells, lyse autologous cells of a subject and/or cause an inflammatory reaction in the absence of an exogenous stimulus. Preferably, the autoimmune disorder is lupus erythematodes (lupus).

The term "immuno-oncological treatment" is also understood by the skilled person. The term preferably relates to the treatment of cancer by modulation of the immune response of a subject. Said modulation may be inducing, enhancing, or suppressing said immune response.

The present invention also relates to a host cell comprising the PD-L1 polypeptide according to the present invention, the polynucleotide according to the present invention, and/or the vector according to the present invention.

As used herein, the term "host cell" relates to any cell capable of receiving and, preferably maintaining and/or expressing, the PD-L1 polypeptide, the polynucleotide and/or the vector of the present invention. More preferably, the host cell is capable of expressing a PD-L1 polypeptide as specified herein encoded on said polynucleotide and/or vector. Preferably, the cell is a bacterial cell, more preferably a cell of a common laboratory bacterial strain known in the art, most preferably an *Escherichia* strain, in particular an *E. coli* strain. Also preferably, the host cell is an eukaryotic cell, preferably a yeast cell, e.g. a cell of a strain of baker's yeast, or is an animal cell. More preferably, the host cell is an insect cell or a mammalian cell, preferably from a mammalian subject as specified herein above, in particular a mouse or rat cell. Most preferably, the host cell is a human cell. It is, however, also envisaged that the host cell is a plant cell.

The present invention also relates to a non-human transgenic organism comprising the host cell of the present invention, the PD-L1 polypeptide according to the present invention, the polynucleotide according to the present invention, and/or the vector according to the present invention.

The term "non-human transgenic organism", as used, relates to any multicellular living being, including in particular plants and animals, except humans. Preferably, the non-human transgenic organism is a subject, preferably a mammalian subject as specified herein above, but not a human subject. Also preferably, the subject is a plant, preferably a monocot or dicot plant.

The present invention also relates to a method for manufacturing a PD-L1 polypeptide according to any one of claims comprising:

(i) expressing the polynucleotide according to the present invention in a host cell; and (ii) obtaining the PD-L1 polypeptide.

The present invention further relates to a PD-L1 polypeptide obtainable by the aforesaid method.

The method for manufacturing a PD-L1 polypeptide, preferably, is an in vitro method. Preferably, the method is performed under GMP and/or GLP conditions. Moreover, the method may comprise further steps, e.g. a step of providing a host cell comprising a suitable expression construct before step (i), and/or one or more purification steps for purifying the PD-L1 polypeptide. Moreover, one or more steps may be assisted or performed by automated equipment.

The present invention also provides for a method of treating and/or preventing organ failure in a subject, in particular a method of treating organ failure in a subject suffering from sepsis, said method comprising (a) administering to said subject a therapeutically effective amount of a PD-L1 polypeptide or (b) administering a therapeutically effective amount of a polynucleotide encoding said PD-L1 polypeptide.

Typical aspects of the invention with respect to the kind of organ failure, the subjects to be treated, sepsis, and the fusion polypeptide or the polynucleotide are described above and apply mutatis mutandis for the present method of treating and/or preventing organ failure in a subject. Preferably, the method encompasses identification of a subject to be treated by determining the presence of sepsis prior to administering the fusion polypeptide or polynucleotide encoding it. Also preferably, the method comprises monitoring the subject for signs of organ failure after administration of the fusion polypeptide and, if necessary, administering the fusion polypeptide or polynucleotide encoding it again or at a difference dosage.

In view of the above, the following embodiments are particularly envisaged:

1. A PD-L1 polypeptide comprising at least a first amino acid sequence at least 70% identical to SEQ ID NO:8, and at least a second sequence at least 70% identical to SEQ ID NO:10, wherein the polypeptide carries an amino acid substitution at least at one of the following positions: V54, Y56, Q63, Q66, V68, A69, P76, I115, A121, D122, Y123, K124, and R125, wherein, if the polypeptide comprises an amino acid substitution at position Y56, C113 or I115, the polypeptide carries at least one further of the aforesaid substitutions; wherein the amino acid positions are based on the murine PD-L1 amino acid sequence (SEQ ID NO 6).
2. A PD-L1 polypeptide comprising at least a first amino acid sequence at least 70% identical to SEQ ID NO:8, and at least a second sequence at least 70% identical to SEQ ID NO:10, wherein the polypeptide carries amino acid substitutions at least at the amino acid positions Y56 and P76, wherein the amino acid positions are based on the murine PD-L1 amino acid sequence (SEQ ID NO:6).
3. A PD-L1 polypeptide comprising at least a first amino acid sequence at least 70% identical to SEQ ID NO:8, and at least a second sequence at least 70% identical to SEQ ID NO:10, wherein the polypeptide carries at least one amino acid substitution in at least one of the following amino acid positions within the first amino acid sequence: V54, Y56, Q63, Q66, V68, A69, P76; and at least one amino acid substitution in at least one of the following amino acid positions within the second amino acid sequence: I115, A121, D122, Y123, K124, and R125, wherein the amino acid positions are based on the murine PD-L1 amino acid sequence (SEQ ID NO:6).
4. The PD-L1 polypeptide of any one of embodiments 1 to 3, wherein said first amino acid sequence is at least 80%, preferably at least 90%, more preferably at least 95% identical to SEQ ID NO:8 and/or wherein said second amino acid sequence is at least 80%, preferably at least 90%, more preferably at least 95% identical to SEQ ID NO:10.
5. The PD-L1 polypeptide of any one of embodiments 1 to 4, wherein the polypeptide comprises at least a first amino acid sequence selected from SEQ ID NO:7 and SEQ ID NO:8, and at least a second sequence selected from SEQ ID NO:9 and SEQ ID NO:10, including said amino acid substitution or substitutions.
6. The PD-L1 polypeptide of any one of embodiments 1 to 5, wherein said polypeptide comprises, preferably consists of, an amino acid sequence at least 70% identical to the amino acid sequence of SEQ ID NO:5.
7. The PD-L1 polypeptide of any one of embodiments 1 to 6, wherein said polypeptide comprises, preferably consists of, an amino acid sequence at least 80%, preferably at least 90%, more preferably at least 95% identical to the amino acid sequence of SEQ ID NO:5
8. The PD-L1 polypeptide of any one of embodiments 1 to 7, wherein said polypeptide comprises, preferably consists of, the amino acid sequence of SEQ ID NO: 4 or SEQ ID NO 5.
9. The PD-L1 polypeptide of any one of embodiments 1 to 8, wherein said polypeptide comprises at least one amino acid substitution at position P76.
10. The PD-L1 polypeptide of any one of embodiments 1 to 9, wherein the polypeptide carries at least one amino acid substitution in at least one of the following amino acid positions within the first amino acid sequence: V54, Y56, Q63, Q66, V68, A69, P76; and at least one amino acid substitution in at least one of the following amino acid positions within the second amino acid sequence: I115, A121, D122, Y123, K124, and R125.

11. The PD-L1 polypeptide of any one of embodiments 1 to 10, wherein the polypeptide carries amino acid substitutions at least at the amino acid positions Y56 and P76.
12. The PD-L1 polypeptide of any one of embodiments 1 to 11, wherein the PD-L1 polypeptide is a variant of PD-L1.
13. The PD-L1 polypeptide of any one of embodiments 1 to 12, wherein the PD-L1 polypeptide carries at least a further substitution at the amino acid position C113.
14. The PD-L1 polypeptide of any one of embodiments 1 to 13, wherein the PD-L1 polypeptide carries at least one further substitution at at least one of the amino acid positions V54, Q66, V68, A69 and/or I115.
15. The PD-L1 polypeptide of any one of embodiments 1 to 14, wherein (i) said Q63 substitution is not a Q63N substitution, (ii) said A69 substitution is not a A69H substitution, (iii) said P76 substitution is not a P76V substitution, and/or (iv) said I115 substitution is not a I115M substitution.
16. The PD-L1 polypeptide of any one of embodiments 1 to 16, wherein (i) said V54 substitution is a V54L substitution, (ii) said Y56 substitution is a Y56G, Y56A, Y56D, or Y56S substitution, (iii) said Q63 substitution is a Q63H substitution, (iv) said Q66 substitution is a Q66R substitution, (v) said V68 substitution is a V68E substitution, (vi) said A69 substitution is a A69T or A69S substitution, (vii) said P76 substitution is a P76F or P76H substitution, and/or (viii) said I115 substitution is a 115L substitution.
17. The PD-L1 polypeptide of any one of embodiments 1 to 16, wherein said polypeptide comprises the substitutions (i) Y56S, P76F, and I115L; (ii) V54L, Y56D, Q66R, V68E, A69S, and P76H; (iii)Y56G, Q63H, P76F, and 115L; (iv) Y56A, Q63H, A69T, and P76F; or (v) Y56A, Q63H, and P76H.
18. The PD-L1 polypeptide of any one of embodiments 1 to 17, wherein the PD-L1 polypeptide comprises, preferably consists of, any of the amino acid sequence as shown in SEQ ID NO:16 to SEQ ID NO:20; preferably wherein the PD-L1 polypeptide comprises, preferably consists of, the amino acid sequence as shown SEQ ID NO:16 or SEQ ID NO:17.
19. The PD-L1 polypeptide of any one of embodiments 1 to 18, wherein the PD-L1 polypeptide is comprised in a fusion polypeptide and/or a polypeptide complex.
20. The PD-L1 polypeptide of any one of embodiments 1 to 19, wherein said fusion polypeptide further comprises at least one polypeptide extending the in vivo half-life of the fusion polypeptide
21. The PD-L1 polypeptide of any one of embodiments 1 to 20, wherein said fusion polypeptide further comprises at least one antibody fragment and/or an ovalbumin or fragment thereof, preferably wherein said fusion polypeptide further comprises an Fc fragment of an immunoglobulin.
22. The PD-L1 polypeptide of any one of embodiments 1 to 21, wherein said polypeptide comprises, preferably consists of, an amino acid sequence as shown in SEQ ID NO:21 or 22, preferably encoded by a polynucleotide comprising the nucleotide sequence of SEQ ID NO:23 or 24.
23. The PD-L1 polypeptide of any one of embodiments 1 to 22, wherein the PD-L1 polypeptide additionally comprises a portion being capable of binding specifically to cytotoxic T-cells, preferably an immunoglobulin or fragment thereof.
24. The PD-L1 polypeptide of embodiment 23, wherein said immunoglobulin is human IgG.
25. The PD-L1 polypeptide of any one of embodiments 1 to 24, wherein said portion capable of binding specifically to cytotoxic T-cells is selected from the group consisting of a polypeptide comprising a portion of the MHC-I complex which is capable of binding to CD8, a portion of the CD80 which is capable of binding to CD28, a polypeptide being an antibody or fragment thereof capable of specifically binding to CD8, a polypeptide being an antibody or fragment thereof capable of specifically binding to CD28,
26. A polynucleotide encoding a PD-L1 polypeptide according to any one of embodiments 1 to 25.
27. The polynucleotide of embodiment 26, wherein the polynucleotide comprises, preferably consists of, a sequence which is at least 60% identical to the sequence shown in SEQ ID NO:1 or SEQ ID NO:2; preferably, the polynucleotide comprises, preferably consists of, a sequence as shown in SEQ ID NO:11 or SEQ ID NO:12.
28. The PD-L1 polypeptide according to any one of embodiments 1 to 25 or the polynucleotide according to embodiment 26 or 27 for use as a medicament.
29. The PD-L1 polypeptide according to any one of embodiments 1 to 25 or the polynucleotide according to embodiment 26 or 27 for use in treating and/or preventing organ failure in a subject suffering from sepsis, for use in treating immune disorders, preferably lupus, and/or for use in immuno-oncological treatment.
30. The PD-L1 polypeptide for use or the polynucleotide for use according to embodiment 29, wherein said organ failure is CD8 cytotoxic T-cell dependent multi-organ failure and/or is caused by an inflammatory reaction, preferably by systemic inflammatory response syndrome (SIRS) or sepsis.
31. The PD-L1 polypeptide for use or the polynucleotide for use according to embodiment 29 or 30, wherein said subject is a mammal, preferably a human.
32. The PD-L1 polypeptide for use or the polynucleotide for use according to any one of embodiments 29 to 31, wherein said polypeptide or polynucleotide upon administration inhibits sepsis-induced cytotoxic T-cells in the subject.
33. The PD-L1 polypeptide for use or the polynucleotide for use according to any one of embodiments 29 to 32, wherein said PD-L1 polypeptide or said polynucleotide upon administration induces a long-lasting tolerance in cytotoxic T-cells in the subject against sepsis-caused activation.
34. A vector comprising the polynucleotide according to embodiment 26 or 27.
35. A host cell comprising the PD-L1 polypeptide according to any one of embodiments 1 to 26, the polynucleotide according to embodiment 26 or 27, and/or the vector according to embodiment 34.
36. A non-human transgenic organism comprising the host cell according to embodiment 35, the PD-L1 polypeptide according to any one of embodiments 1 to 26, the polynucleotide according to embodiment 26 or 27, and/or the vector according to embodiment 34.
37. A method for manufacturing a PD-L1 polypeptide according to any one of embodiments comprising:
(i) expressing the polynucleotide according to embodiment 26 or 27 in a host cell; and
(ii) obtaining the PD-L1 polypeptide.

38. A PD-L1 polypeptide obtainable by the method of embodiment 37.

All references cited in this specification are herewith incorporated by reference with respect to their entire disclosure content and the disclosure content specifically mentioned in this specification.

FIGURES

FIG. 1: Competitive Phage ELISA. 5 PD-L1 variants (214, 243, 291, 246 and 258) and unmodified PD-L1 wt were displayed on phage and tested for binding to surface immobilized PD-1 (black). In a similar experiment binding was competed with either 50 nM (dark grey) or 500 nM (light grey) of PD-1 in solution to approximate binding affinities. Recorded signal corresponds to optical density (OD) at 450 nm.

Figure 2:
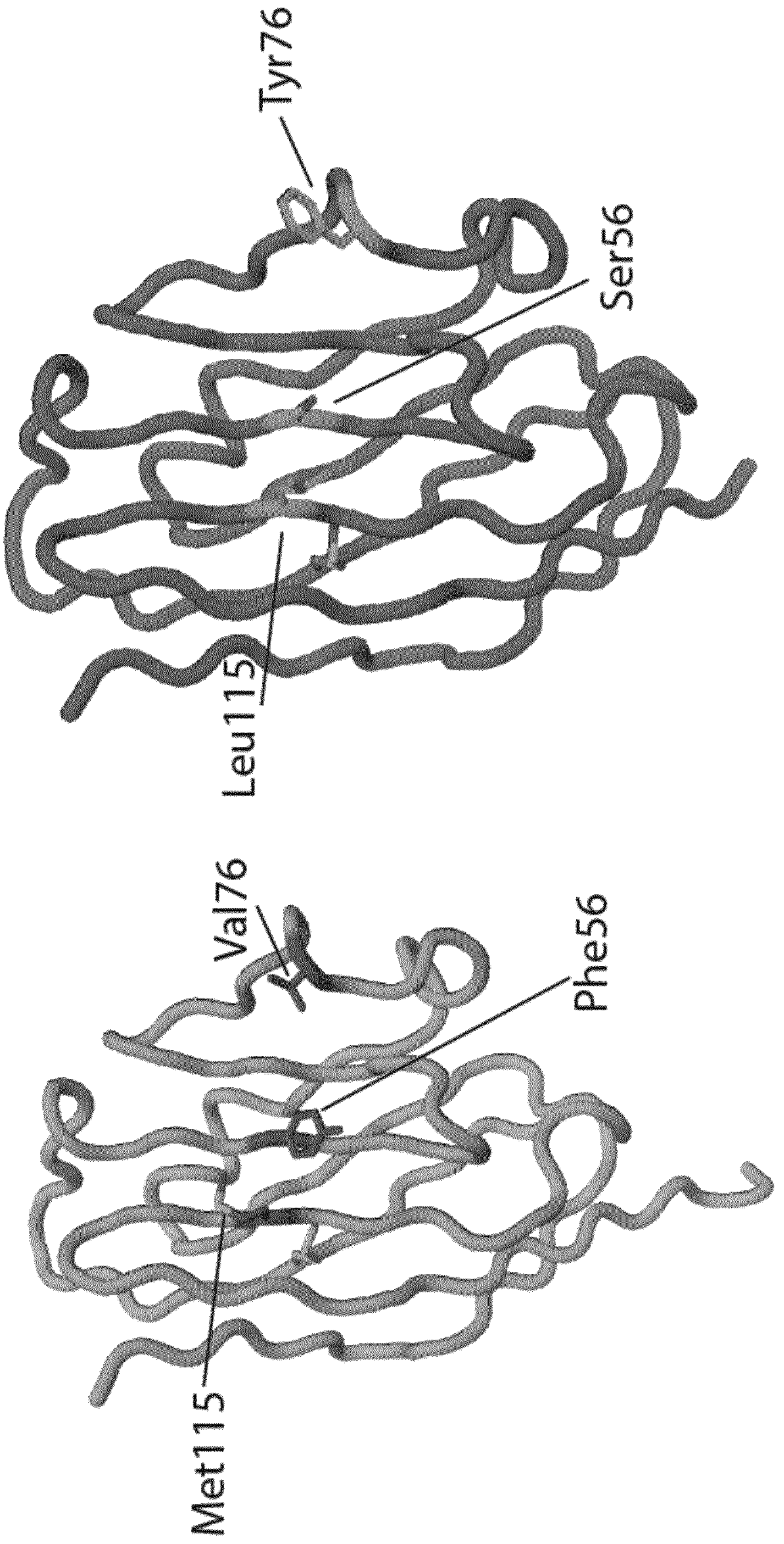
Figure 2:
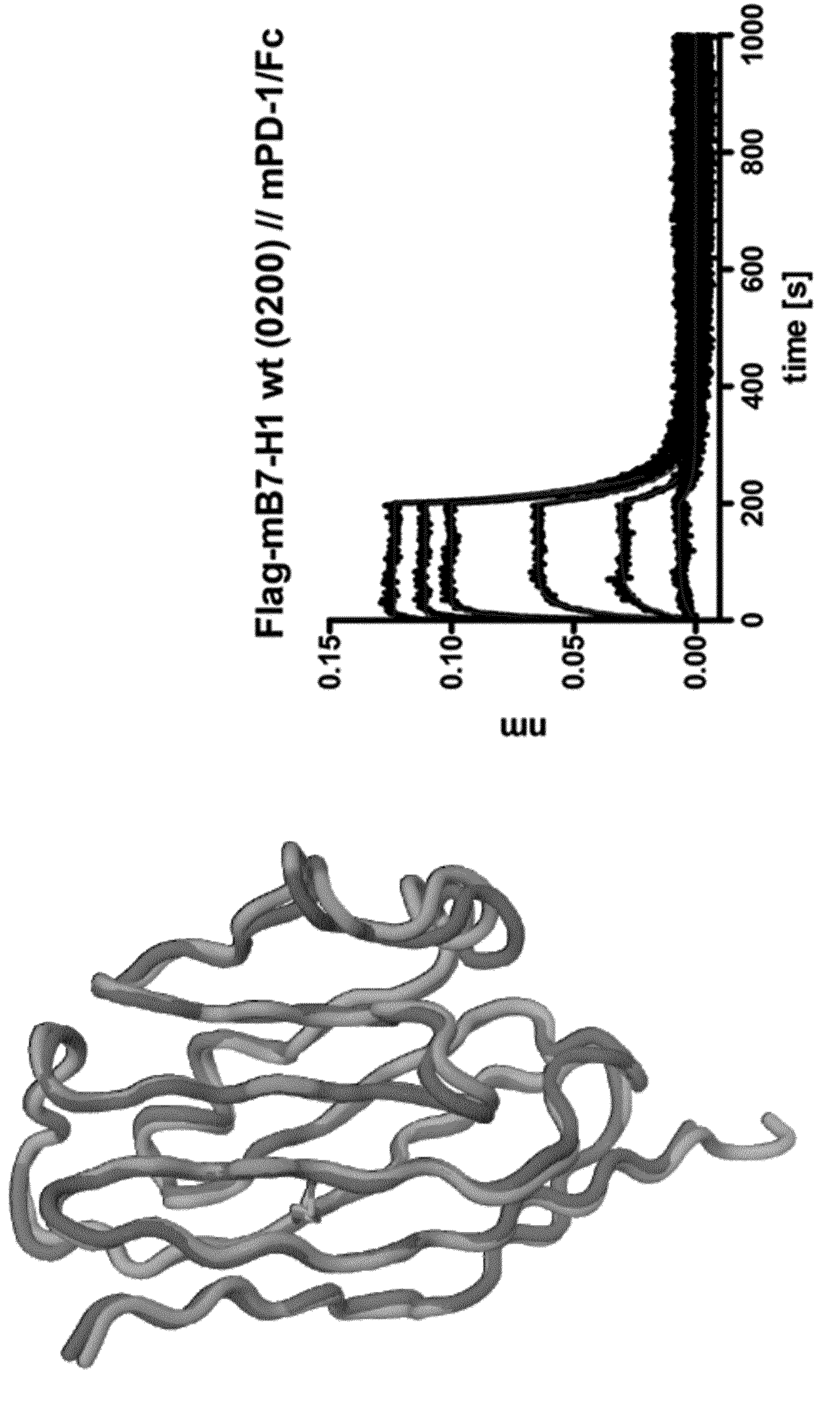
Figure 2:
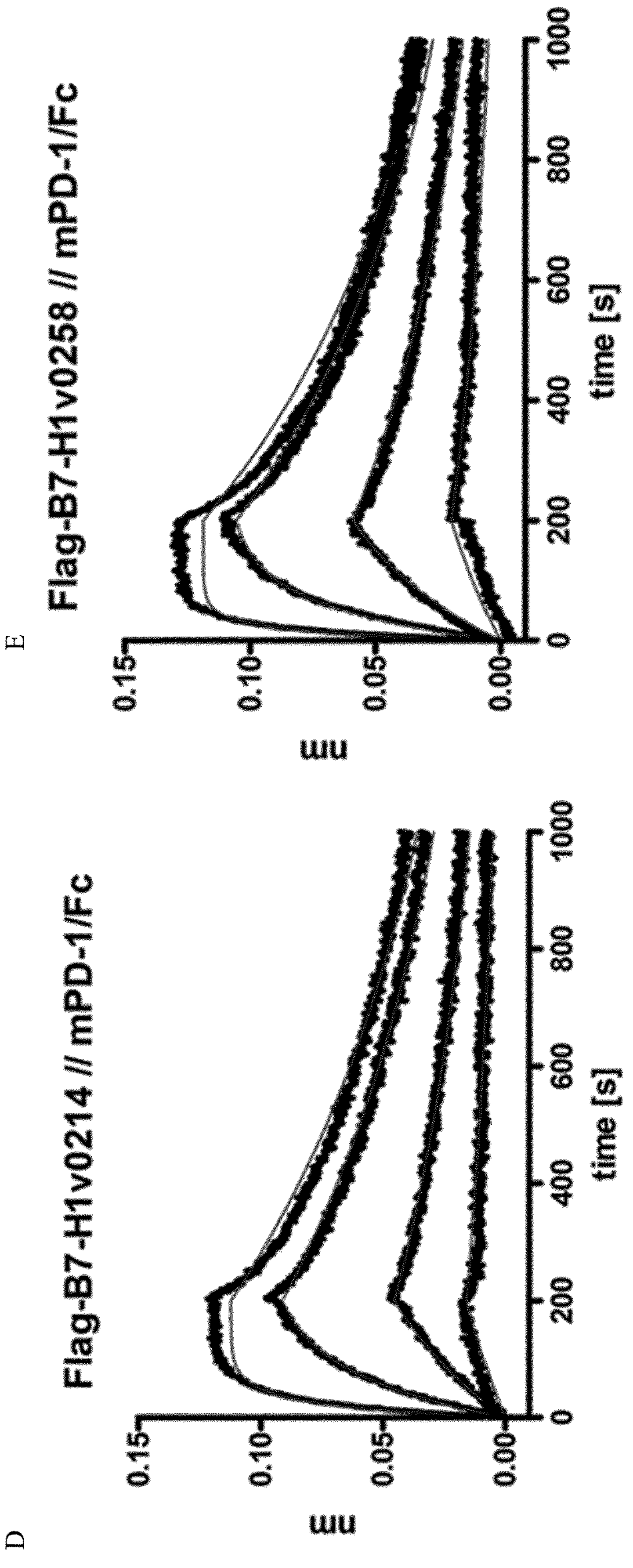

FIG. 2: Structural comparison of PD-L1 variant 0258 with PD-L1 Ig variable domain (PDB: 3BIK). (A) Side-by-side comparison of the amino-acid positions in wt PD-L1 (left panel) that have been mutated in clone 0258 (right panel). Amino acids are indicated and shown as sticks. (B) Structural alignment indicates an identical structural conformation. (C)-(E) Representative bio-layer interferometry sensograms for PD-L1 wt (C) and two indicated engineered PD-L1 variants (D, E). Raw data (thick lines) was fitted using 1:1 langmuir interaction model (thin lines).

Figure 3:
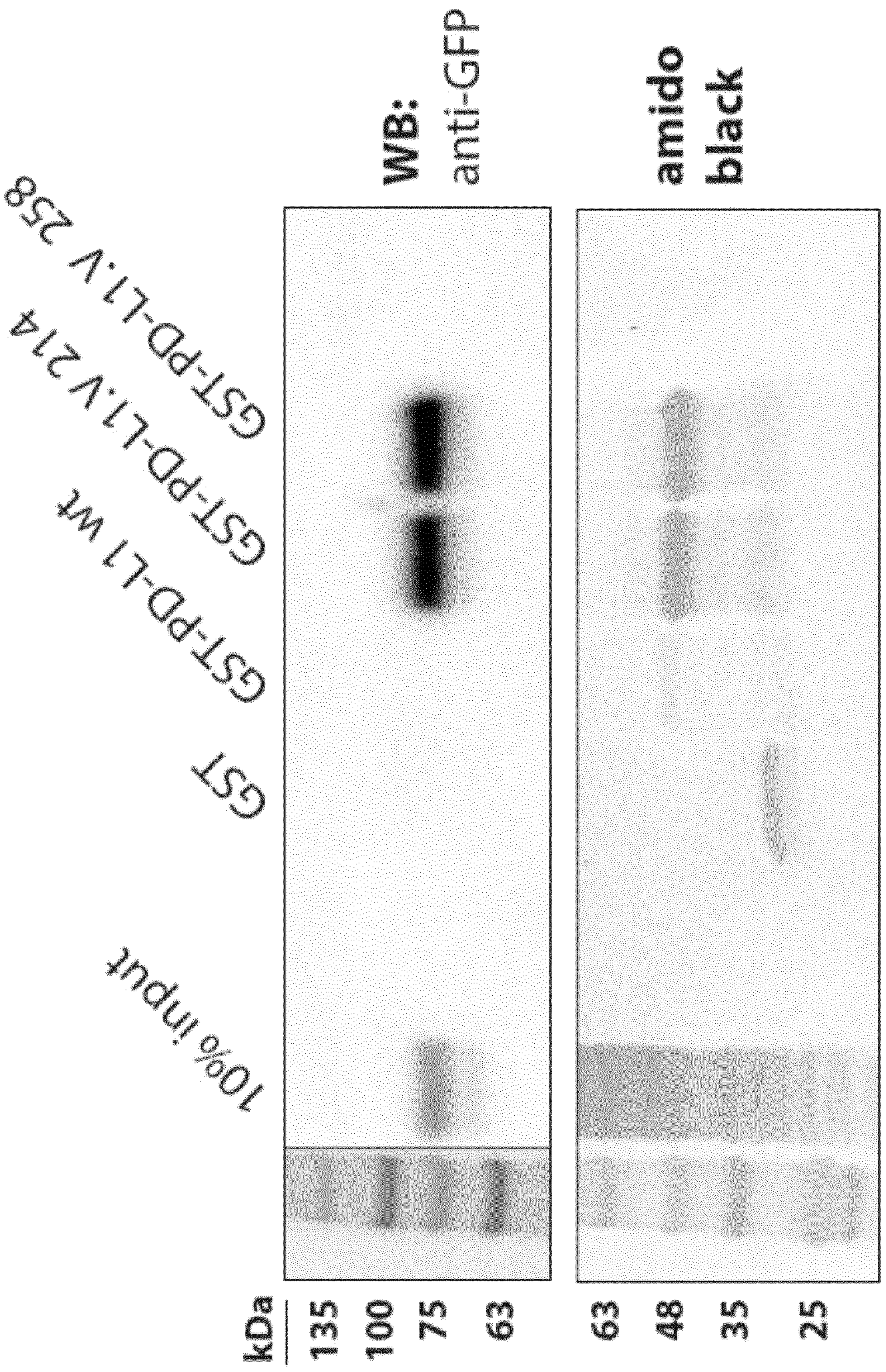

FIG. 3: Pull-down experiment with GST fusions of distal Ig-like domain of PD-L1 wild type and two engineered variants (214 and 258). Bacterially expressed GST fusions were immobilized on glutathione beads and incubated with cell lysate of Jurkat cells stably expressing murine PD-1-EGFP construct. WB—Western blot.

Figure 4:
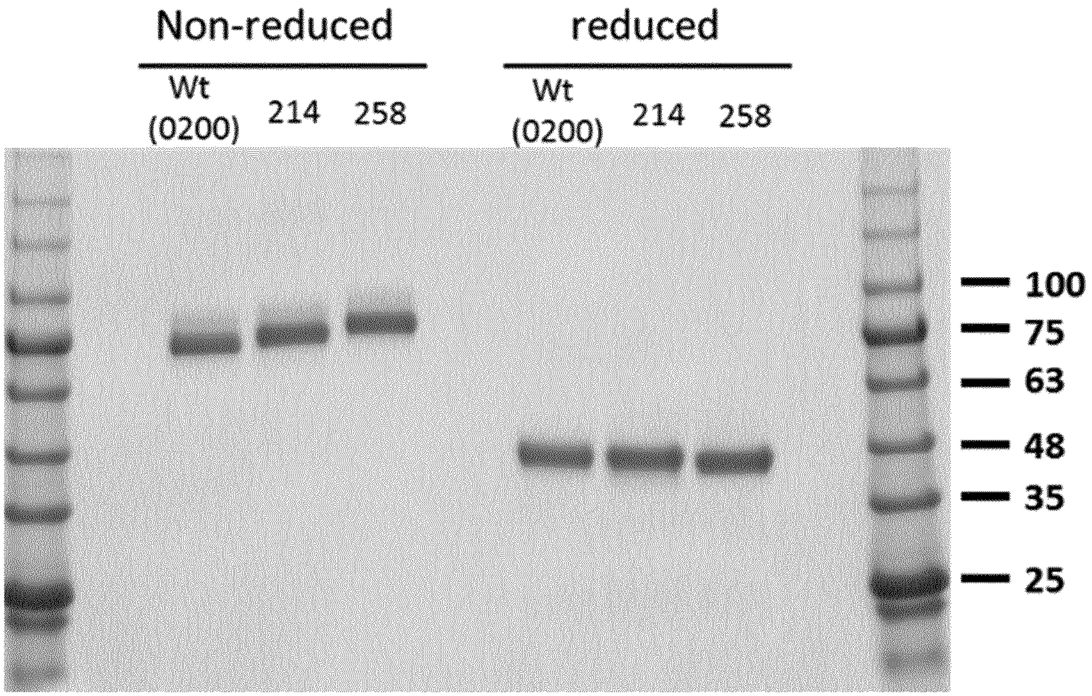
Figure 4:
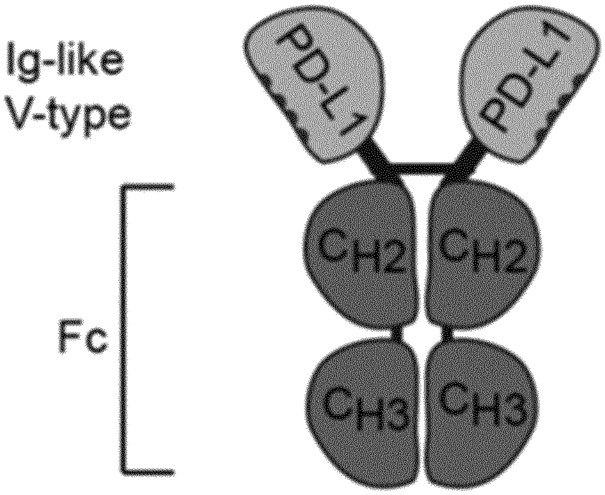

FIG. 4: Fc-fusion protein of the Ig-like V-type domain of PD-L1. (A) SDS-Page analysis of purified PD-L1-Fc fusion protein. From left to right: non-reduced, i.e. disulfide linked dimer (78 kDa) and reduced monomer (39 kDa) of wt (200) and two engineered PD-L1 variants (214 and 258). (B) Domain arrangement of disulfide linked dimer of PD-L1 Fc fusion proteins.

Figure 5:
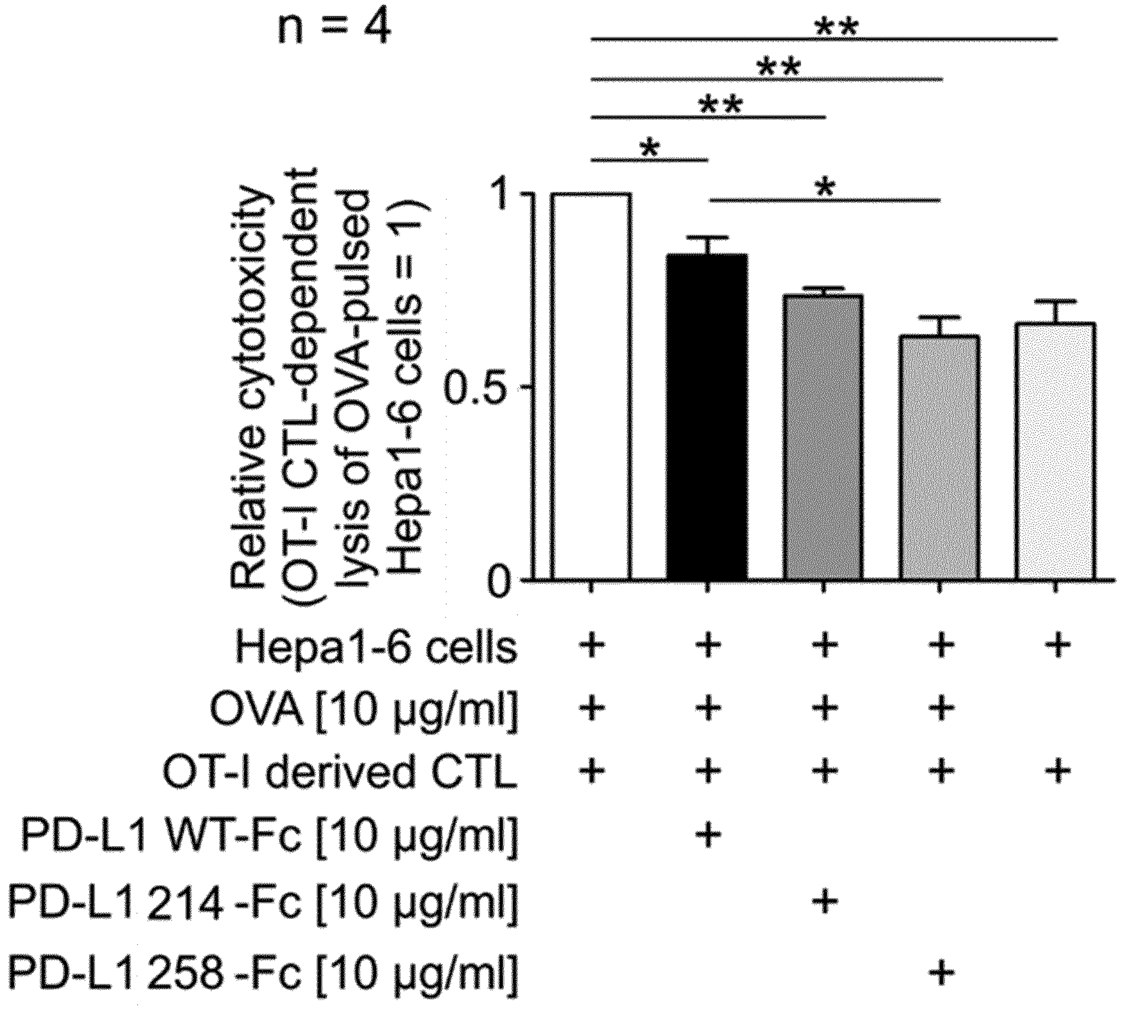

FIG. 5: Recombinant PD-L1-Fc chimera prevents CTL-dependent cytotoxicity. Cytotoxic T cell-dependent hepatocyte killing was determined using Hepa1-6 cells as target cells and CD8+ T cells derived from OT-I mice as effector cells. CellTrackerOrange stained Hepa1-6 cells were pulsed for two hours with the OVA257-264 peptide. Afterwards, Hepa1-6 cells were co-cultured with enriched CD8+ T cells derived from the spleen of OT-I mice at a ratio of 5:1 (effector: target cells). In parallel, recombinant PD-L1-Fc chimera (WT, 214 and 258) were added at the indicated concentrations. The number of surviving target cells was examined by FACS analysis. Data from four independent experiments are provided. Data represent the means±SD (*$p<0.05$, **$p<0.01$).

Figure 6:
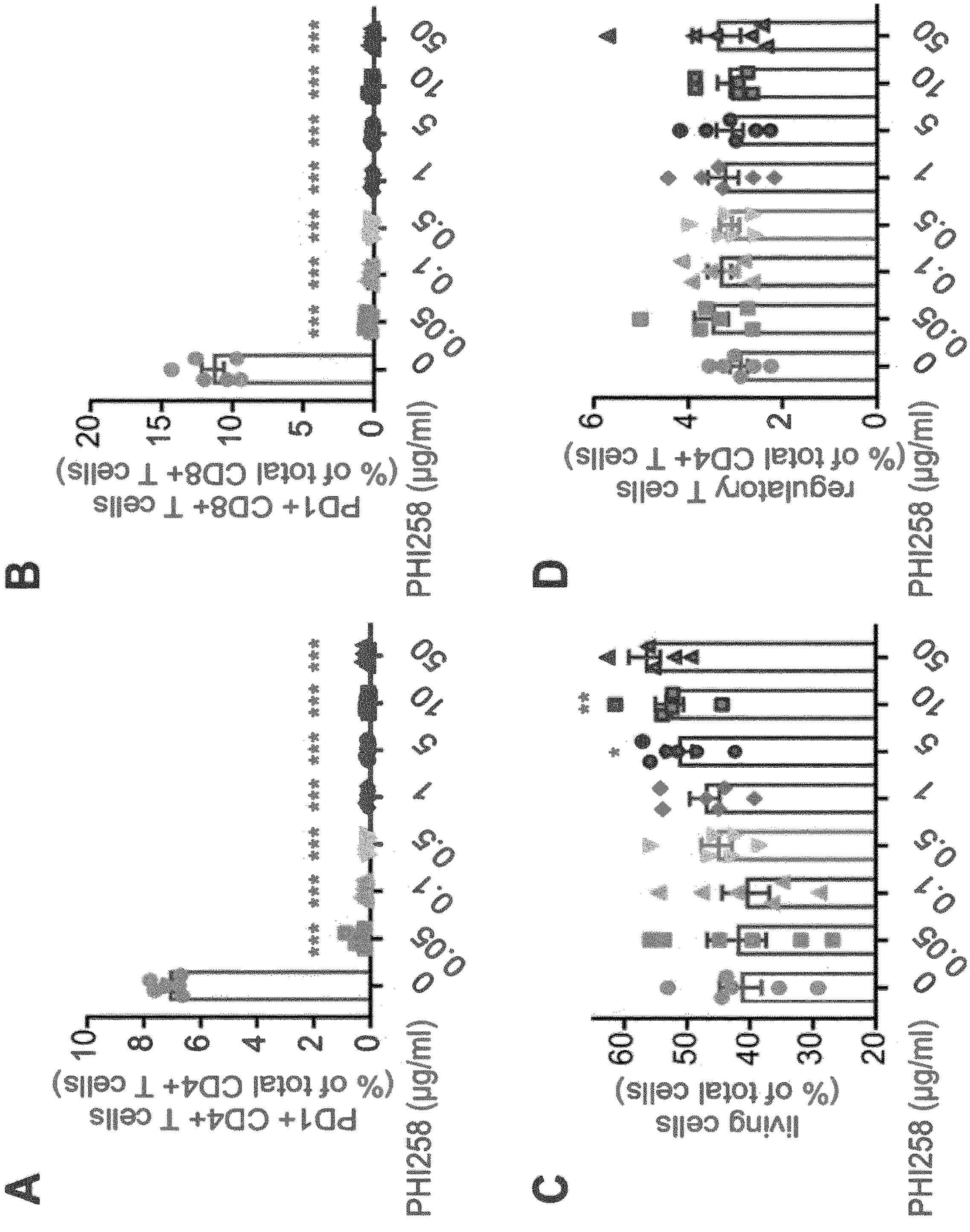

FIG. 6. Impact of PHI258 on cell parameters during MLR. PBMCs from four Buffy Coats were isolated and PBMCs of two donors ($2\times10^5$ each) were co-cultured in T cell medium for 6 days with or without addition of PHI258 at different concentrations (50 ng/ml-50 μg/ml) on day 0. Afterwards, cells were analyzed by flow cytometry. (A,B) Expression of PD-1 on CD4+(A) and CD8+(B) T cells. (C) Living cells within the total cell populations. (D) $CD127^{low}$ $CD25^{high}$ T regs with total CD4+ T cells. Individual data points and means±SEM are shown. Dunn's multiple comparison test. *$p<0.05$; $p<0.01$; *$p<0.001$.

Figure 7:
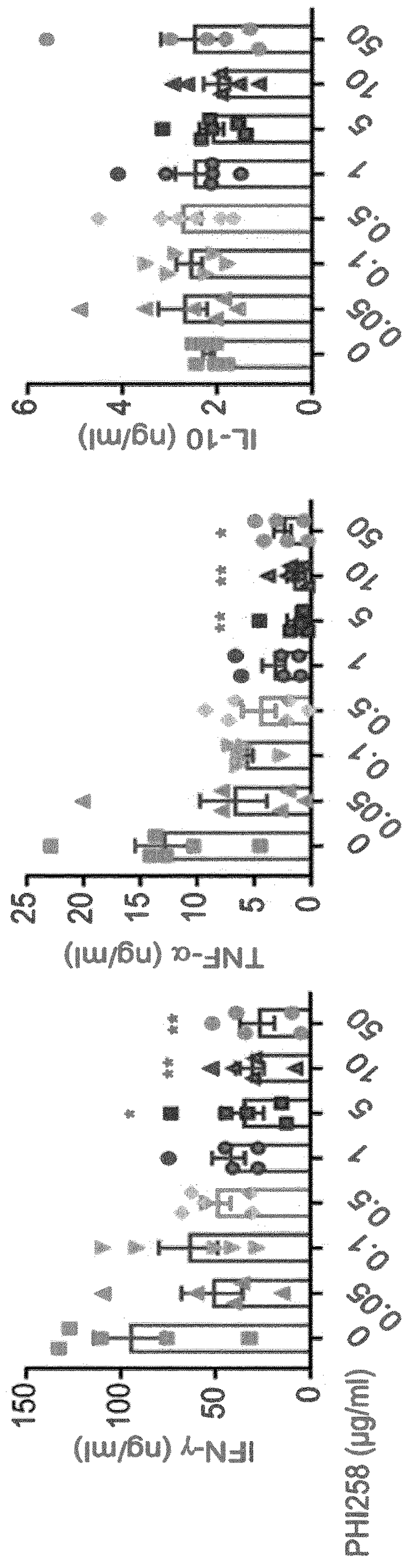

FIG. 7. Impact of PHI258 on cytokine production during MLR. PBMCs from four Buffy Coats were isolated and PBMCs of two donors ($2\times10^5$ each) were co-cultured in T cell medium for 6 days with or without addition of PHI258 at different concentrations (50 ng/ml-50 μg/ml) on day 0. Cytokine levels in supernatants were analyzed at day 6 by Cytometric Bead Array. Individual data points and means±SEM are shown. Dunn's multiple comparison test. *$p<0.05$; **$p<0.01$.

Figure 8:
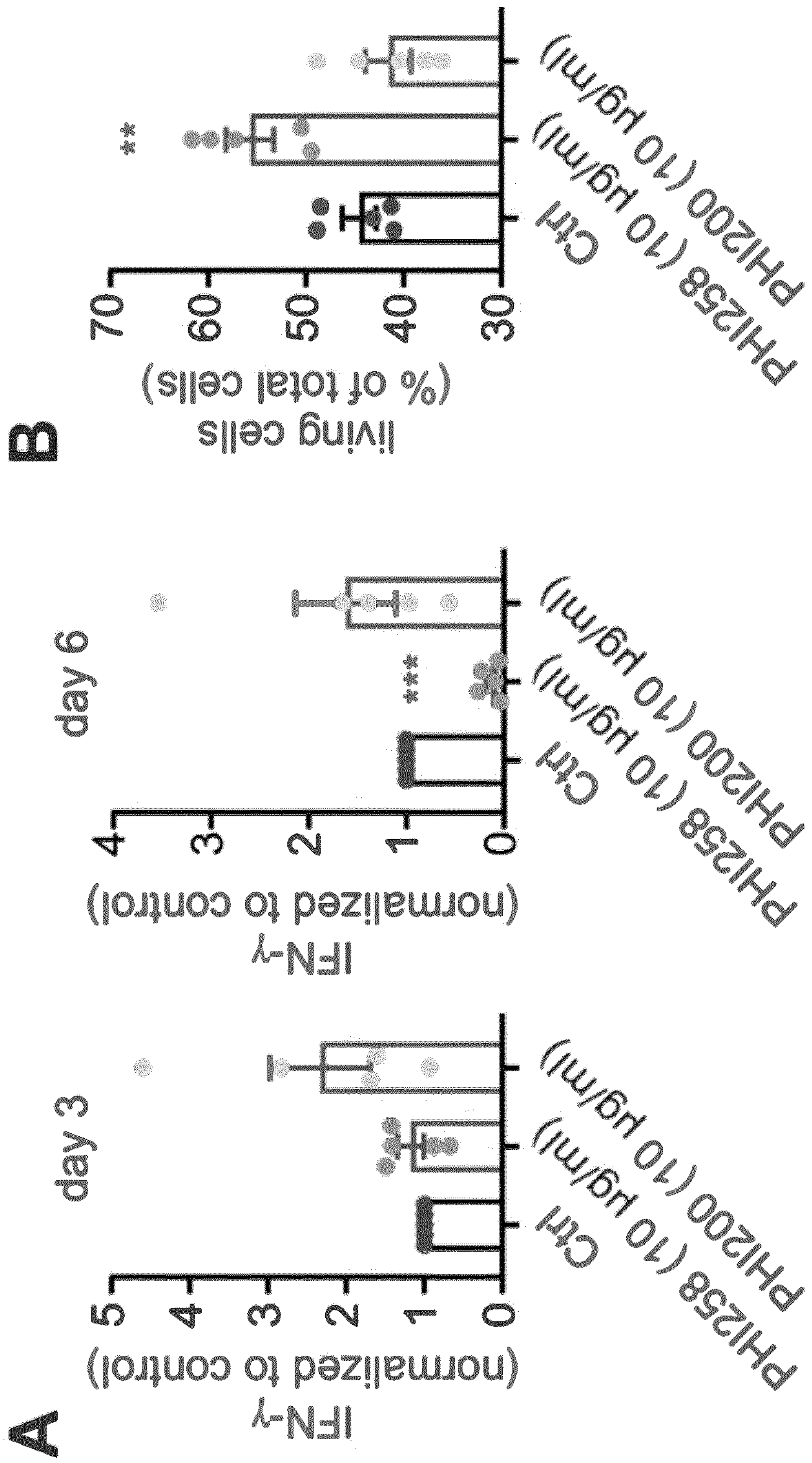

FIG. 8. PHI258 versus PHI200 (wildtype) during MLR. PBMCs from four Buffy Coats were isolated and PBMCs of two donors ($2\times10^5$ each) were co-cultured in T cell medium for 6 days with or without addition of PHI258 or PHI200 (10 μg/ml each) on day 0. (A) Cytokine levels in supernatants were analyzed by Cytometric Bead Array and living cells within the total cell populations were determined by FACS. Individual data points and means±SEM are shown. Dunn's multiple comparison test. $p<0.01$; *$p<0.001$.

EXAMPLES

The invention will be merely illustrated by the following Examples. The said Examples shall, whatsoever, not be construed in a manner limiting the scope of the invention.

Example 1

A library of $2\times10^9$ mutants of PD-L1 displayed on the surface of filamentous phage M13 was constructed. Using a published structure of a crystal complex of wild type PD-1 and PD-L1 as a guide, we engineered only the distal Ig-like domain of PD-L1 (amino acids 18-132 on murine PD-L1) and, in order to improve display levels, we additionally introduced a C113R mutation in the murine PD-L1 moiety prior to library construction. Based on the crystal structure, we selected 14 amino acid residues of PD-L1 for randomization that are buried in the interface and make side-chain contacts to PD-1.

Phage selections were performed using as an antigen recombinant murine PD-1 protein (amino acids 31-150) with C83S substitution fused to AviTag peptide, biotinylated in vivo and purified from *E. coli*. After a couple of selection rounds, binding of enriched phage clones were analyzed by ELISA and the selected PD-L1 variants were sequenced. In a competitive phage $IC_{50}$ ELISA, the 5 PD-L1 variants were examined for their binding properties by competing with 500 nM or 50 nM in solution with PD-1-Fc (FIG. 1). All 5 clones were chosen for further characterization and expressed as His-tag fusions in *E. coli* The sequences of the selected variants and their affinity towards PD-1-Fc (measured by bio-layer interferometry, BLI, on an Octet device) indicated that the variants 214 and 258 had an up to 30 fold advantage in binding to surface-immobilized murine PD-1Fc compared to PD-L1 wt expressed in the same format.

Tables 1 and 2 show amino acid sequence and affinity of selected PD-L1 variants. Amino acid positions 54, 56, 63, 66, 68, 69, 76, 113, 115, and 121-125 were randomized. For the selected variants, dashes represent no amino acid change relative to the wild type sequence. Kd values for the interaction of the variants and murine PD-1 were obtained by bio-layer interferometry; n/a—not available. Table 2 indicates R113 because the original C113 of the murine sequence was substituted already prior to library construction, as indicated above.

TABLE 1

| | | region 1 | | | | | | | | | | | | | | | | | | | | | | |
|---|---|---|---|---|---|---|---|---|---|---|---|---|---|---|---|---|---|---|---|---|---|---|---|---|
| wt | Kd [nM] 66 | 54 V | 55 V | 56 Y | 57 W | 58 E | 59 K | 60 E | 61 D | 62 E | 63 Q | 64 V | 65 I | 66 Q | 67 F | 68 V | 69 A | 70 G | 71 E | 72 E | 73 D | 74 L | 75 K | 76 P |
| 246 | n/a | — | — | G | — | — | — | — | — | — | H | — | — | — | — | — | — | — | — | — | — | — | — | F |
| 243 | n/a | — | — | A | — | — | — | — | — | — | H | — | — | — | — | — | T | — | — | — | — | — | — | F |
| 214 | 2.54 | L | — | D | — | — | — | — | — | — | — | — | — | R | — | E | S | — | — | — | — | — | — | H |
| 258 | 2.17 | — | — | S | — | — | — | — | — | — | — | — | — | — | — | — | — | — | — | — | — | — | — | F |
| 291 | n/a | — | — | A | — | — | — | — | — | — | H | — | — | — | — | — | — | — | — | — | — | — | — | H |

TABLE 2

| | | region 2 | | | | | | | | | | | | |
|---|---|---|---|---|---|---|---|---|---|---|---|---|---|---|
| wt | Kd [nM] 66 | 113 R | 114 C | 115 I | 116 I | 117 S | 118 Y | 119 G | 120 G | 121 A | 122 D | 123 Y | 124 K | 125 R |
| 246 | n/a | — | — | L | — | — | — | — | — | — | — | — | — | — |
| 243 | n/a | — | — | — | — | — | — | — | — | — | — | — | — | — |
| 214 | 2.54 | — | — | — | — | — | — | — | — | — | — | — | — | — |
| 258 | 2.17 | — | — | L | — | — | — | — | — | — | — | — | — | — |
| 291 | n/a | — | — | — | — | — | — | — | — | — | — | — | — | — |

Clones 0258 (also referred to as PHI258 below) and 0214 were further analyzed. Representative BLI sensograms for these two variants are shown in FIG. 2. The low RMSD value of 0.762 Å$^2$ of the structural overlay of clone 0258 with the PD-L1 Ig-like variable domain indicates that the mutations do not alter the native conformation. This result indicates that the increase in affinity is due to optimization of intramolecular contacts and not due to changes in the binding topology of clone 0258 to PD-1 relative to the unmodified PD-L1 Ig-like variable domain (FIG. 2A, B, C). Furthermore, using lysates of Jurkat cells stably expressing murine PD-1-EGFP fusion construct, we performed a pull-down assay using wt PD-L1 and the variants 0214 and 0258. Both engineered variants interact with PD-I-EGFP much more strongly than the wild type construct or the GST control (FIG. 3).

Meanwhile, we have cloned and expressed the PD-L1 variants as fusion proteins with human Fc for expression in mammalian cells. The establishment of PD-L1 wt and PD-L1 variants as Fc-fusion protein improves high bioavailability in subsequent in vivo experiments. Additionally, a mammalian expression system allows the optimal formation of intramolecular disulfide-bridges at a better yield than bacteria.

After expression and purification of the Fc fusion proteins, we obtained with one step purification on a protein A column, good purity and an average yield of 200 mg/L Expi293F culture (FIG. 4). In order to verify whether the purified protein is still binding the PD-1, we determined PD-1/PD-L1 affinities as before. Because of the binding avidity caused by the dimerization of the Fc fusions, the affinity of the variants showed an increase in binding from 2.54 and 2.14 nM to 88 and 77 pM, respectively. In similar experiments, we observed an affinity of ~600 pM for the wt protein, indicating that the PD-L1 variants have an up to ~8-fold improved affinity for PD-1 in vitro.

We validated the immunosuppressive action of the PD-L1 Fc fusion proteins by testing the cytotoxicity of T-cells in presence of the variants and wt control. Cytotoxic T cells were derived from OT-1 mice which are sensitive to the presentation of ovalbumin derived peptides by MHC on the surface mouse cells. To induce T-cell activity, a mouse derived hepatocyte cell line Hepa1 was pulsed with ovalbumin and the cytotoxicity was measured by monitoring cell death by FACS (FIG. 5).

Example 2

To analyze the impact of PHI258 (i.e. PD-L1 variant 258 described above) on allogeneic lymphocyte activation in a human setting, we performed mixed lymphocyte reaction (MLR) assays using PBMCs from Buffy Coats of healthy anonymous human blood donors. PBMCs of two donors each were mixed and maintained in T cell growth medium for up to 6 days with or without addition of PHI258 at different concentrations (50 ng/ml-50 μg/ml).

First, cells were analyzed by flow cytometry on day 6 to determine PD-1 expression on CD4+ and CD8+ T cells. Incubation with PHI258 even at very low doses strongly interfered with the detection of PD-1 on the surface of both T cell subsets (FIG. 6A, B), indicating either competition of binding to PD-1 with the FACS antibody or PD-1 internalization. Next, the proportion of living cells as a function of the MLR was determined. PHI258 significantly increased the number of living cells at concentrations >5 μg/ml (FIG. 6C). Thus, PHI258 likely prevented cell killing during MLR. The relative cell composition was unchanged, as exemplarily shown in FIG. 6D for regulatory T cells.

Next, cytokine production indicating leukocyte activation during MLR was determined by Cytometric Bead Array. PHI258 significantly suppressed the secretion of the pro-inflammatory cytokines IFN-γ and TNF-α at concentrations >5 μg/ml, while the effect at lower concentrations was more heterogeneous (FIG. 7). Importantly, PHI258 did not suppress the production of the anti-inflammatory cytokine IL-10 (FIG. 7).

PD-1 is upregulated upon T cell activation, which occurs ~3 days after T cell activation. To analyze of PD-1 expression was required for PHI258 to act, IFN-γ levels at day 3 and day 6 during MLR were compared. Moreover, unmodified PD-L1 (PHI200) was used as a control. Neither PHI258 or PHI200 affected IFN-γ levels at day 3. However, PHI258, but not PHI200 strongly suppressed IFN-γ levels at day 6

(FIG. 8A). Corresponding to its lack of efficacy in limiting inflammatory cytokine production, PHI200 also did not affect cell viability in MLR cultures in contrast to PHI258 (FIG. 8B).

In conclusion, PHI258 bound to PD-1 on human T cells with high efficacy in MLR cultures and suppressed inflammatory cytokine levels and cell killing, while not suppressing anti-inflammatory features such as IL-10 expression and regulatory T cell levels.

LITERATURE CITED

Hotchkiss and Opal (2010) *N Engl J Med* 363:87-89
Meisel et al. (2009) Am J Respir Crit Care Med 180:640-648
Otto et al. (2011) Crit Care 15:R183
Reinhart et al. (2001) Crit Care Med 29:765-769
Vincent, et al. (2013) Lancet 381:774-775
von Knethen et al. (2019), Theranostics 9(7):2003
WO 2017/029389 A1

The invention claimed is:

1. A PD-L1 polypeptide comprising an amino acid sequence at least 95% identical to SEQ ID NO: 4 or SEQ ID NO: 5, wherein the polypeptide carries amino acid substitutions at least at the amino acid positions Y56 and P76, wherein said P76 substitution is not a P76V substitution, and wherein the PD-L1 polypeptide carries at least one further substitution at at least one of the amino acid positions V54, Q63, Q66, V68, A69 and/or I115, wherein the amino acid positions are based on the murine PD-L1 amino acid sequence (SEQ ID NO:6), and wherein the PD-L1 polypeptide binds to PD-1 with a Kd of at most 50 nM.

2. The PD-L1 polypeptide of claim 1, wherein the PD-L1 polypeptide carries at least a further substitution at the amino acid position C113.

3. The PD-L1 polypeptide of claim 1, wherein (i) said V54 substitution is a V54L substitution, (ii) said Y56 substitution is a Y56G, Y56A, Y56D, or Y56S substitution, (iii) said Q63 substitution is a Q63H substitution, (iv) said Q66 substitution is a Q66R substitution, (v) said V68 substitution is a V68E substitution, (vi) said A69 substitution is a A69T or A69S substitution, (vii) said P76 substitution is a P76F or P76H substitution, and/or (viii) said I115 substitution is a I115L substitution.

4. The PD-L1 polypeptide of claim 1, wherein said polypeptide comprises the substitutions (i) Y56S, P76F, and I115L;

(ii) V54L, Y56D, Q66R, V68E, A69S, and P76H;

(iii) Y56G, Q63H, P76F, and I115L;

(iv) Y56A, Q63H, A69T, and P76F; or (v) Y56A, Q63H, and P76H.

5. The PD-L1 polypeptide of claim 1, wherein the PD-L1 polypeptide comprises any of the amino acid sequence as shown in SEQ ID NO: 16 to SEQ ID NO: 20.

6. The PD-L1 polypeptide of claim 1, wherein the PD-L1 polypeptide is comprised in a fusion polypeptide and/or a polypeptide complex.

7. The PD-L1 polypeptide of claim 1, wherein said polypeptide comprises, an amino acid sequence as shown in SEQ ID NO: 21 or 22.

8. A polynucleotide encoding a PD-L1 polypeptide according to claim 1.

9. A method of treating and/or preventing organ failure in a subject suffering from sepsis and/or of treating an immune disorder in a subject, wherein the immune disorder is lupus, said method comprising (a) administering to said subject a therapeutically effective amount of the PD-L1 polypeptide according to claim 1 or (b) administering to said subject a therapeutically effective amount of a polynucleotide encoding the PD-L1 polypeptide according to claim 1.

10. The method of claim 9, wherein said organ failure is caused by an inflammatory reaction.

11. A host cell comprising the PD-L1 polypeptide according to claim 1.

12. The method of claim 10, wherein said inflammatory reaction is systemic inflammatory response syndrome (SIRS) or sepsis.

13. The PD-L1 polypeptide of claim 6, wherein said fusion polypeptide further comprises at least one antibody fragment and/or an ovalbumin or fragment thereof.

14. The PD-L1 polypeptide of claim 6, wherein said fusion polypeptide further comprises an Fc fragment of an immunoglobulin.

15. The PD-L1 polypeptide of claim 7, wherein said polypeptide is encoded by a polynucleotide comprising the nucleotide sequence of SEQ ID NO: 23 or 24.

* * * * *